United States Patent
Andersson et al.

(10) Patent No.: US 6,716,834 B2
(45) Date of Patent: Apr. 6, 2004

(54) THIOCHROMANE DERIVATIVES AND THEIR USE AS THROMBIN INHIBITORS

(75) Inventors: Kjell Andersson, Mölndal (SE); Tord Inghardt, Mölndal (SE); Olle Karlsson, Mölndal (SE); Marcel Linschoten, Huddinge (SE); Jan-Erik Nyström, Södertälje (SE); Gunnel Sundén, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/276,150
(22) PCT Filed: May 14, 2001
(86) PCT No.: PCT/SE01/01052
  § 371 (c)(1),
  (2), (4) Date: Nov. 12, 2002
(87) PCT Pub. No.: WO01/87879
  PCT Pub. Date: Nov. 22, 2001

(65) Prior Publication Data
US 2003/0220317 A1 Nov. 27, 2003

(30) Foreign Application Priority Data
May 16, 2000 (SE) .............................. 0001803-6

(51) Int. Cl.⁷ ....................... A61K 31/395; A61P 43/00; C07D 205/08
(52) U.S. Cl. ................... 514/210.02; 540/362
(58) Field of Search ........... 540/362; 514/210.02

(56) References Cited

U.S. PATENT DOCUMENTS

| | | |
|---|---|---|
| 4,346,078 A | 8/1982 | Bajusz et al. |
| 4,703,036 A | 10/1987 | Bajusz et al. |
| 5,260,307 A | 11/1993 | Ackermann et al. |
| 5,405,854 A | 4/1995 | Ackermann et al. |
| 5,559,232 A | 9/1996 | Ackermann et al. |
| 6,030,972 A | 2/2000 | Bohm et al. |
| 6,440,937 B1 | 8/2002 | Baucke et al. |
| 6,455,671 B1 | 9/2002 | Bohm et al. |

FOREIGN PATENT DOCUMENTS

| | | |
|---|---|---|
| EA | 0 362 002 A1 | 4/1990 |
| EP | 0 195 212 A2 | 9/1986 |
| EP | 0 195 212 | 9/1986 |
| EP | 0 293 881 A2 | 12/1988 |
| EP | 0 364 344 A2 | 4/1990 |
| EP | 0 364 344 A3 | 4/1990 |
| EP | 0 526 877 A2 | 2/1993 |
| EP | 0 530 167 A1 | 3/1993 |
| EP | 0 542 525 A2 | 5/1993 |
| EP | 0 648 780 A1 | 4/1995 |
| EP | 0 669 317 A1 | 8/1995 |
| EP | 0 994 104 A1 | 4/2000 |
| GB | 2 161 801 A | 1/1986 |
| WO | WO 93/11152 | 8/1993 |
| WO | WO 93/18060 | 9/1993 |
| WO | WO 94/29336 | 12/1994 |
| WO | WO 95/23609 | 9/1995 |
| WO | WO 96/03374 | 2/1996 |
| WO | WO 96/31504 | 10/1996 |
| WO | WO 96/32110 | 10/1996 |
| WO | WO 97/02284 | 1/1997 |
| WO | WO 97/23499 | 7/1997 |
| WO | WO 97/33576 | 9/1997 |
| WO | WO 97/33576 A1 | 9/1997 |
| WO | WO 97/39770 | 10/1997 |
| WO | WO 97/46577 | 12/1997 |
| WO | WO 97/49404 | 12/1997 |
| WO | WO 98/57932 | 12/1998 |
| WO | WO 98/57934 | 12/1998 |
| WO | WO 99/00356 | 1/1999 |
| WO | WO 99/29664 | 6/1999 |
| WO | WO 00/35869 | 6/2000 |
| WO | WO 00/35869 A1 | 6/2000 |
| WO | WO 00/66152 | 11/2000 |

OTHER PUBLICATIONS

Abdel–Wahab et al., "Modern Friedel–Crafts Chemistray. XI. Cyclization of Aryl Haloalkyl Sulfones, Arylsulfonylacyl Chlorides and Their Corresponding Sulfides," Phosphorus and Sulfur, vol. 19, pp. 31–44 (1984).

(List continued on next page.)

Primary Examiner—Joseph K. McKane
Assistant Examiner—Andrea D. Small
(74) Attorney, Agent, or Firm—Ropes & Gray LLP

(57) ABSTRACT

There is provided compounds of formulae I and IA

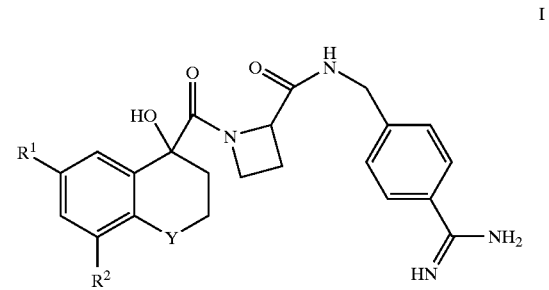

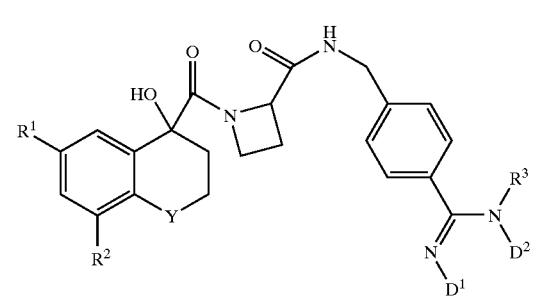

wherein Y, $R^1$, $R^2$, $R^3$, $D^1$ and $D^2$ have meanings given in the description which are useful as, or as prodrugs of, competitive inhibitors of trypsin-like proteases, such as thrombin, and in particular in the treatment of conditions where inhibition of thrombin is required (e.g. thrombosis) or as anticoagulants.

15 Claims, No Drawings

OTHER PUBLICATIONS

Stephan et al., "Effect of Tertatolol and of Its Metabolites and Structural Analogues in Isolated Perfused Rat Kidney Vasculature," Journal of Cardiovascular Pharmacology, vol. 16, 338–346 (1990).

Blomback et al., "Synthetic Peptides with Anticoagulant and Vasodilating Activity," Scand. J. clin. Lab. Invest. Suppl. 107, 59–64 (1969).

Goran Claeson, "Synthetic peptides and peptidomimetics as substrates and inhibitors of thrombin and other proteases in the blood coagulation system," Blood Coagulation and Fibrinolysis, vol. 5, 411–436 (1994).

Ofosu et al., "Inhibition of factor X and factor V activation by dermatan sulfate and a pentasaccharide with high affinity for antithrombin III in human plasma," (1990).

Lyon et al., "Evaluation of the thrombin inhibitor D–phenylalanyl–L–prolyl–L–arginine chloromethylketone (PPACK) with the factor Xa inhibitor 1,5–dansyl–L–glutamyl–L–glycyl–L–arginine chlormethylketone (GGACK) as anticoagulants for critical care clinical chemistry specimens," Clinica Chimica Acta 280, 91–99 (1999).

Elg, et al., "Effects of Agents, Used to Treat Bleeding Disorders, on Bleeding Time Prolonged by a Very High Dose of a Direct Thrombin Inhibitor in Anesthesized Rats and Rabbits," Thrombosis Research 101, 159–170 (2001).

Kawasaki, et al., "Effect of a Synthetic Factor Xa Inhibitor, YM–60828, on Blood Vessel Patency in Combination with a Thrombolytic Agent and on Blood Loss from the Operation Site in a Rat Model of Arterial Thrombosis," Thromb Haemost 79, 859–64 (1998).

THIOCHROMANE DERIVATIVES AND THEIR USE AS THROMBIN INHIBITORS

This application is a national stage filing under 35 U.S.C. 371 of PCT application PCT/SE01/01052, filed May 14, 2001, which claims priority from Sweden Application No. 0001803-6, filed May 16, 2000, the specifications of each of which are incorporated by reference herein. PCT Application PCT/SE01/01052 was published under PCT Article 21(2) in English.

FIELD OF THE INVENTION

This invention relates to novel pharmaceutically useful compounds, in particular compounds that are, or are prodrugs of, competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

Further, it is known that administration of prodrugs of thrombin inhibitors may give rise to improvements in:

(a) certain pharmacokinetic properties after administration of; and
(b) the prevalence of certain side effects associated with, those inhibitors.

PRIOR ART

The early development of low molecular weight inhibitors of thrombin has been described by Claesson in Blood Coagul. Fibrinol. (1994) 5, 41 1.

Blombäck et al (in J. Clin. Lab. Invest. 24, suppl. 107, 59, (1969)) reported thrombin inhibitors based on the amino acid sequence situated around the cleavage site for the fibrinogen ƒ chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an ƒcs-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position (International Patent Application WO 97/23499 discloses prodrugs of certain of these compounds); European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidino-piperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl ƒ-keto esters and amides, European Patent Application 0 362 002 fluoroalkylamide ketones, European Patent Application 0 364 344 ƒ,ƒ,ƒ-triketocompounds, and European Patent Application 0 530 1675 ƒ-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609, WO 96/25426, WO 97/02284, WO 97/46577, WO 96/32110, WO 96/31504, WO 96/03374, WO 98/06740, WO 97/49404 and WO 99/29664. Certain prodrugs of thrombin inhibitors have been disclosed in WO 97/33576.

WO 98/57932 and WO 00/35869 disclose thrombin inhibitors, and prodrugs of thrombin inhibitors, based on peptidyl derivatives with fused, bi- or tri-cyclic acids at the P3-position.

However, there remains a need for effective inhibitors of trypsin-like serine proteases, such as thrombin. There is, also a need for compounds that have a favourable pharmacokinetic profile (e.g. low clearance), are orally bioavailable, and are selective in inhibiting thrombin over other serine proteases, in particular those involved in haemostatis. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided compounds of formula I,

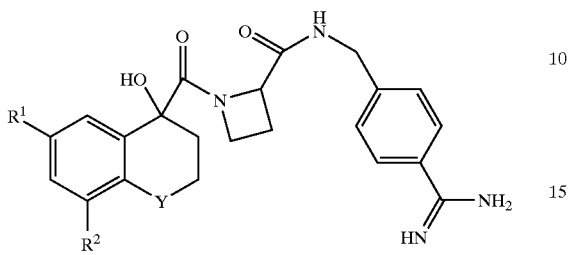

wherein

Y represents S(O) or S(O)$_2$;

R$^1$ represents halo; and

R$^2$ represents H, halo or C$_{1-4}$ alkoxy (which latter group is optionally substituted by one or more halo groups);

or a pharmaceutically acceptable derivative thereof, which compounds are referred to hereinafter as "the compounds of the invention".

The term "pharmaceutically acceptable derivatives" of compounds of formula I includes pharmaceutically acceptable salts. Suitable salts include inorganic acid (e.g. hydrogen halide), and organic acid (e.g. acetic, methanesulfonic or trifluoroacetic acid), addition salts.

The alkyl part of alkoxy groups which R$^2$ may represent, may, when there is a sufficient number of carbon atoms, be linear or branched, be saturated or unsaturated, be cyclic, acyclic or part cyclic/acyclic, and/or be optionally interrupted by an O atom.

Halo groups which R$^1$ and R$^2$ may represent, and with which R$^2$ may be substituted, include fluoro, chloro, bromo and iodo.

Abbreviations are listed at the end of this specification.

Compounds of the invention that may be mentioned include those in which Y represents S(O)$_2$.

Preferred compounds of the invention include those in which:

R$^1$ represents chloro;

R$^2$ represents H, halo or C$_{1-2}$ alkoxy (which latter group is optionally substituted by one or more halo (e.g. fluoro) groups).

More preferred compounds of the invention include those in which:

R$^1$ represents chloro; and

R$^2$ represents H, chloro, OCHF$_2$, OCF$_3$ or, especially, OCH$_3$.

Preferred compounds of formula I include the compounds of the Examples described hereinafter, particularly the compound of Example 1.

According to the invention there is also provided a process for the preparation of compounds of formula I which comprises:

(i) the coupling of a compound of formula III,

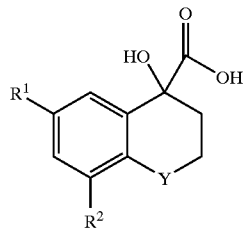

wherein Y, R$^1$ and R$^2$ are as hereinbefore defined, with 4-amidinobenzyl-2-azetidinecarboxamide (see, for example, international patent application WO 97/02284), for example in the presence of a coupling agent (e.g. EDC, DCC, HBTU, HATU, TBTU, PyBOP or oxalyl chloride in DMF), an appropriate base (e.g. pyridine, 2,4,6-collidine, DMAP, TEA or DIPEA) and a suitable organic solvent (e.g. dichloromethane, acetonitrile or DMF);

(ii) the coupling of a compound of formula IV,

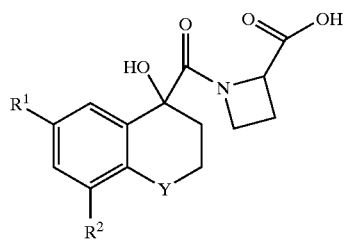

wherein Y, R$^1$ and R$^2$ are as hereinbefore defined, with para-amidino-benzylamine, for example in the presence of a coupling agent (e.g. oxalyl chloride in DMF, EDC, DCC, HBTU, HATU, PyBOP or TBTU), an appropriate base (e.g. pyridine, DMAP, TEA, 2,4,6-collidine or DIPEA) and a suitable organic solvent (e.g. dichloromethane, acetonitrile or DMF); or (iii) complete oxidation (for compounds of formula I in which Y is S(O)$_2$), or partial oxidation (for compounds of formula I in which Y is S(O)), of a corresponding compound of formula V,

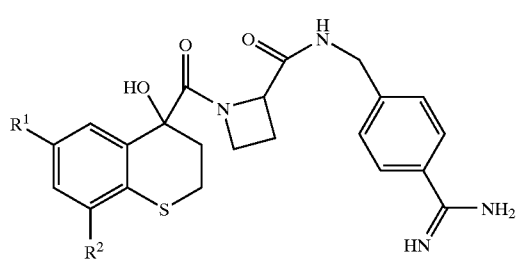

wherein R$^1$ and R$^2$ are as hereinbefore defined, for example in the presence of an appropriate amount of a suitable oxidising agent (e.g. mCPBA, hydrogen peroxide or potassium peroxymonosulfate) and an appropriate organic solvent (e.g. CH$_2$Cl$_2$, methanol, water or mixtures thereof), and optionally in the presence of a suitable protic acid (e.g. acetic acid).

The skilled person will appreciate that, in the case of partial oxidation, a mixture of stereoisomers may be obtained, which may be separated by techniques known to those skilled in the art (e.g. by column chromatography or chiral chromatography).

Compounds of formula III may be prepared by complete or partial oxidation of a compound of formula VI,

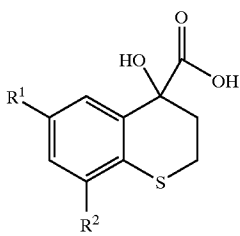

VI wherein $R^1$ and $R^2$ are as hereinbefore defined, for example under conditions such as those described hereinbefore for the synthesis of compounds of formula I (process step (iii)).

Compounds of formula IV may be prepared by the coupling of a compound of formula III, as hereinbefore defined, with azetidine-2-carboxylic acid, for example under conditions such as those described hereinbefore for synthesis of compounds of formula I (see, for example, process steps (i) and (ii)).

Compounds of formula IV may alternatively be prepared by complete or partial oxidation of a compound of formula VII,

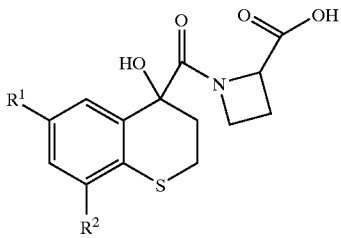

VII wherein $R^1$ and $R^2$ are as hereinbefore defined, for example under conditions such as those described hereinbefore for the synthesis of compounds of formula I (process step (iii)).

Compounds of formula V may be prepared in accordance with peptide coupling techniques, for example in analogous fashion to the methods described hereinbefore for compounds of formula I (see, for example, process steps (i) and (ii)). If desired, compounds of formula VII may also be prepared in this way.

Compounds of formula VI are available using known and/or standard techniques.

For example, compounds of formula VI may be prepared by reaction of a compound of formula VIII,

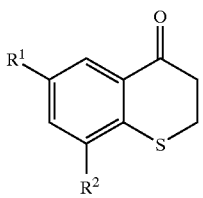

VIII wherein $R^1$ and $R^2$ are as hereinbefore defined, with:

(a) a compound of formula IX,

IX wherein R" represents H or $(CH_3)_3Si$, for example at room, or elevated, temperature (e.g. below 100° C.) in the presence of a suitable organic solvent (e.g. chloroform or dichloromethane) and, if necessary, in the presence of a suitable base (e.g. TEA) and/or a suitable catalyst system (e.g. benzylammonium chloride or zinc iodide), followed by hydrolysis in the presence of an acid (e.g. HCl or $H_2SO_4$), for example at 20° C. (e.g. according, or analogously, to the method described by C. F. Bigge et al. in J. Med. Chem. (1993) 36, 1977), and then followed by hydrolysis under alkaline conditions (e.g. in the presence of water and either lithium or potassium hydroxide) to give the free acid;

(b) NaCN or KCN, for example in the presence of $NaHSO_3$ and water, followed by hydrolysis; or (c) chloroform, for example at elevated temperature (e.g. above room temperature but below 100° C.) in the presence of a suitable base (e.g. sodium hydroxide) and, if necessary, in the presence of a suitable catalyst system (e.g. benzylammonium chloride), followed by hydrolysis.

The enantiomeric forms of compounds of formula VI (i.e. those compounds having different configurations of substituents about the C-atom that is in the α-position relative to the $CO_2H$ group) may be separated by techniques known to those skilled in the art (e.g. by chromatography, using a chiral chromatographic medium).

Compounds of formula VI may alternatively be prepared by way of a Sharpless stereoselective dihydroxylation of a compound of formula X,

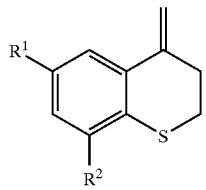

X wherein $R^1$ and $R^2$ are as hereinbefore defined, under conditions known to those skilled in the art (e.g. at low temperature (e.g. 0° C.), using, for example, the commercial reagent AD-mix-b™ in the presence of suitable solvent (e.g. t-butanol), followed by oxidation of the resultant intermediate (e.g. at elevated temperature (e.g. 75° C.) in the presence of a stream of air and Pt/C (5%) in acetone/water).

Compounds of formula VIII are available using known and/or standard techniques. For example, compounds of formula VIII may be prepared by cyclisation of a compound of formula XI,

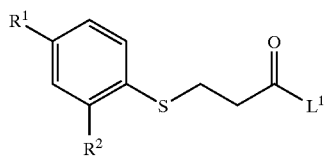

XI wherein $L^1$ represents a leaving group such as OH, $C_{1-4}$ alkoxy, $C_{1-4}$ acyloxy (optionally substituted by one or more halo atoms) or halo and $R^1$ and $R^2$ are as hereinbefore defined, for example in the presence of a suitable catalyst (e.g. trifluoroacetic anhydride, a protic acid such as $H_2SO_4$ or a Lewis acid such as $BF_3$) and optionally in the presence of an appropriate solvent (e.g. $CH_2Cl_2$).

Compounds of formula XI may be prepared in accordance with known techniques. For example, compounds of formula XI may be prepared by reaction of a compound of formula XII,

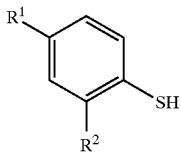

XII wherein $R^1$ and $R^2$ are as hereinbefore defined, with a compound of formula XIII,

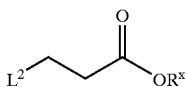

XIII wherein $L^2$ represents a leaving group such as halo and $R^x$ represents $C_{1-6}$ alkyl, for example at between room and reflux temperature in the presence of an appropriate base (e.g. triethylamine or $Cs_2CO_3$) and a suitable solvent (e.g. ethyl acetate or acetone), followed by conversion of the ORX group into an $L^1$ group under conditions that are well known to those skilled in the art (e.g. for compounds of formula XI in which $L^1$ represents OH, by hydrolysis under alkaline conditions).

Compounds of formulae IX, X, XII and XIII, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions (e.g. as described hereinafter).

The compounds of formula I may be isolated from their reaction mixtures using conventional techniques.

Substituents on the aromatic ring in compounds of formulae I, III, IV, V, VI, VII, VIII, X, XI and XII may be introduced and/or interconverted using techniques well known to those skilled in the art. For example, halo may be introduced, both into the aromatic ring and into the alkyl part of alkoxy groups that $R^2$ may represent, by reaction with suitable halogenating agents, for example as described hereinafter.

In accordance with the present invention, pharmaceutically acceptable derivatives of compounds of formula I also include "protected" derivatives of compounds of formula I and/or compounds that act as prodrugs of compounds of formula I.

In this respect, according to a further aspect of the invention there is provided derivatives of compounds of formula I as defined herein which are compounds of formula IA,

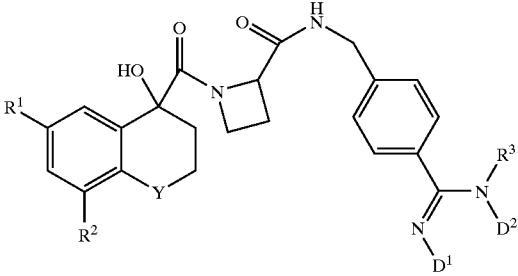

IA wherein
Y, $R^1$ and $R^2$ are as hereinbefore defined;
$D^1$ and $D^2$ independently represent H, —$OR^7$ or $R^8$, or $D^1$, $D^2$ and $R^3$, together with the amidine group to which they are attached, form a cyclic group of formula IIa, IIb, IIc, IId or IIe,

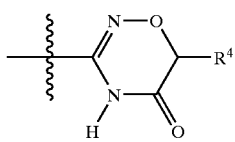

IIa

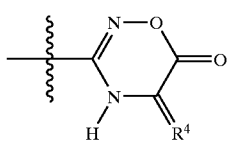

IIb

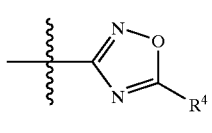

IIc

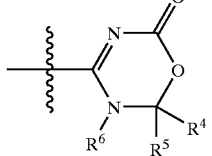

IId

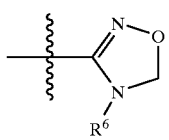

IIe wherein wavy lines indicate the points of attachment to the benzene ring;
$R^3$ represents H, or $R^3$, $D^1$, and $D^2$ together with the amidine group to which they are attached, form a cyclic group of formula IIa, IIb, IIc, IId or IIe;
$R^4$ and $R^5$ independently represent H or $C_{1-4}$ alkyl;
$R^6$ represents H, $C_{1-6}$ alkyl (which latter group is optionally substituted by one or more halo groups) or C(O) $OR^{12}$;
$R^7$ represents H, $C_{6-10}$ aryl, $C_{1-10}$ alkyl (which latter group is optionally substituted by one or more halo groups), $C_{1-3}$ alkylphenyl, —$C(R^{9a})(R^{9b})R^{10}$, —$C(O)R^{11a}$, —$C(O)O^{12}$, —$C(O)N(R^{13})R^{14}$ or —$(CH_2)_n(O)_mR^{15}$;

$R^8$ represents —C($R^{9a}$)($R^{9b}$)$R^{10}$, —C(O)$R^{11b}$ or —C(O)O$R^{12}$;

$R^{9a}$ and $R^{9b}$ independently represent, at each occurrence, H or $C_{1-6}$ alkyl;

$R^{10}$ represents, at each occurrence, —OC(O)$R^{16a}$, —OC(O)O$R^{17}$, —N($R^{18a}$)C(O)O$R^{17}$ or —OC(O)N($R^{18b}$)$R^{17}$;

$R^{11a}$ and $R^{11b}$ independently represent, at each occurrence, $C_{6-10}$ aryl, $C_{1-3}$ alkylphenyl (which latter two groups are optionally substituted by one or more substituents selected from $C_{1-6}$ alkyl and halo), —[C($R^{19a}$)($R^{19b}$)]$_p$OC(O)$R^{16b}$, or $R^{11a}$ represents $C_{1-17}$ alkyl (optionally substituted by $C_{1-6}$ alkoxy, $C_{1-6}$ acyloxy, amino or halo) or $R^{11b}$ represents $C_{1-6}$ alkyl;

$R^{12}$ represents, at each occurrence, $C_{1-17}$ alkyl (optionally substituted by one or more substituents selected from $C_{1-6}$ alkoxy, $C_{1-6}$ acyloxy, —Si($R^{20a}$)($R^{20b}$)($R^{21c}$) and halo), $C_{6-10}$ aryl, $C_{1-3}$ alkylphenyl (which latter two groups are optionally substituted by $C_{1-6}$ alkyl, $C_{1-6}$ alkoxy, cyano or halo), —[C($R^{19a}$)($R^{19b}$)]$_q$OC(O)$R^{16b}$ or —$CH_2R^{21}$;

$R^{13}$ represents H or $C_{1-7}$ alkyl, or together with $R^{14}$ represents $C_{4-5}$ alkylene;

$R^{14}$ represents $C_{6-10}$ aryl or $C_{1-10}$ alkyl (which latter group is optionally substituted by one or more substituents selected from OH, halo, $CO_2H$, $C_{1-6}$ alkoxy, $C_{1-6}$ acyloxy and $C_{6-10}$ aryl), or together with $R^{13}$ represents $C_{4-5}$ alkylene;

$R^{15}$ represents $C_{1-7}$ alkyl optionally substituted by one or more —OC(O)C(H)($R^{22}$)N(G)($G^a$) groups;

$R^{16a}$, $R^{16b}$ and $R^{17}$ independently represent, at each occurrence, $C_{6-10}$ aryl or $C_{1-17}$ alkyl (which latter group is optionally substituted by one or more substituents selected from —OH, halo, —$CO_2H$, $C_{1-6}$ alkoxy, $C_{1-6}$ acyloxy and $C_{6-10}$ aryl), or $R^{16b}$ represents $C_{1-6}$ alkoxy (optionally substituted by one or more substituents selected from $C_{1-6}$ alkyl and halo);

$R^{11a}$ and $R^{11b}$ independently represent H or $C_{1-4}$ alkyl;

$R^{19a}$ and $R^{19b}$ independently represent, at each occurrence, H or $C_{1-6}$ alkyl;

$R^{20a}$ to $R^{20c}$ independently represent, at each occurrence, $C_{1-6}$ alkyl or phenyl;

$R^{21}$ represents the structural fragment IIf

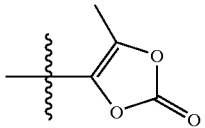

IIf $R^{22}$ represents $C_{3-4}$ alkyl;

G and $G^a$ independently represent H, an amino protective group, or G and $G^a$ together represent an amino protective group;

m represents 0 or 1;

n represents 1, 2 or 3;

p represents 3 or 4;

q represents 2 or 3;

or a pharmaceutically acceptable salt thereof, provided that:

(a) $D^1$ and $D^2$ do not both represent H; and (b) when one of $D^1$ and $D^2$ represents —$OR^7$, then the other represents H.

Suitable "pharmaceutically acceptable salts" of compounds of formula IA include inorganic acid (e.g. hydrogen halide), and organic acid (e.g. acetic, methanesulfonic or trifluoroacetic acid), addition salts.

The compounds of the invention may exhibit tautomerism. All tautomeric forms and mixtures thereof are included within the scope of the invention. Particular tautomeric forms that may be mentioned include those connected with the position of the double bond in the amidine functionality, and the position of the substituent $D^1$ or $D^2$, in compounds of formula IA.

For the avoidance of doubt, in compounds of formula IA, substituents $D^1$ and $D^2$ are completely independent of each other. For example, $D^1$ and $D^2$ may both be represented by $R^8$ in which, in both cases, $R^8$ represents —C(O)$R^{11b}$ in which $R^{11b}$ represents, in both cases, $C_{1-6}$ alkyl. However, in such instances the $C_{1-6}$ alkyl group may be the same of different.

The compounds of formulae I and IA also contain at least two asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

As used herein, the term "aryl" includes phenyl, naphthyl (e.g. 2-naphthyl) and the like. Unless otherwise indicated, aryl groups are optionally substituted by one or more substituents selected form $C_{1-6}$ alkyl and halo.

Alkyl and alkylene groups, as well as alkyl parts of alkoxy, alkylphenyl and acyloxy groups, in compounds of formula IA may, when there is a sufficient number of carbon atoms, be linear or branched, be saturated or unsaturated, be cyclic, acyclic or part cyclic/acyclic, and/or be optionally interrupted by an O atom. The skilled person will appreciate that, when alkyl groups in compounds of formula IA are cyclic and interrupted by oxygen, they may then represent oxygen-containing heterocycles such as tetrahydrofuranyl or (where appropriate) tetrahydropyranyl.

Halo groups in compounds of formula IA include fluoro, chloro, bromo and iodo.

As used herein, the term "amino protective group" includes groups mentioned in "Protective Groups in Organic Synthesis", $2^{nd}$ edition, T W Greene & P G M Wutz, Wiley-Interscience (1991), in particular those indexed at the start of the chapter entitled "*Protection for the Amino Group*" (see pages 309 to 315) of that reference, the disclosure in which document is hereby incorporated by reference.

Specific examples of amino protective groups thus include:

(a) carbamate groups (e.g. methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-trimethylsilylethyl, 2-methylthioethyl, 2-methylsulfonylethyl, 2(p-toluenesulfonyl)ethyl, 2-phosphonioethyl, 1,1-dimethylpropynyl, 1,1-dimethyl-3-(N,N-dimethylcarboxamido)-propyl, 1,1-dimethyl-3-(N,N-diethylamino)propyl, 1-methyl-1-(1- adamantyl)ethyl, 1-methyl-1-phenylethyl, 1-methyl-1-(3,5-dimethoxyphenyl)ethyl, 1-methyl-1-(4-biphenylyl)ethyl, 1-methyl-1-(p-phenylazophenyl) ethyl, 1,1-dimethyl-2-haloethyl, 1,1-dimethyl-2,2,2-trichloroethyl, 1,1-dimethyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4,6-tri-t-butylphenyl, m-nitrophenyl, S-phenyl, 8-quinolinyl, N-hydroxypiperidinyl, 4-(1,4-dimethylpiperidinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitrobenzyl, o-nitrobenzyl, 3,4-dimethoxy-6-nitrobenzyl, p-bromobenzyl, chlorobenzyl, 2,4-dichloro-benzyl, p-cyanobenzyl, o-(N,N-dimethylcarboxamidobenzyl) benzyl, m-chloro-p-acyloxybenzyl, p-(dihydroxyboryl) benzyl, p-(phenylazo)benzyl, p-(p'-methoxyphenylazo) benzyl, 5-benzisoxazolylmethyl, 9-anthrylmethyl, diphenylmethyl, phenyl(o-nitrophenyl)methyl, di(2-pyridyl)methyl, 1-methyl-1-(4-pyridyl)-ethyl, isonicotinyl or S-benzyl carbamate groups);

(b) amide groups (e.g. N-formyl, N-acetyl, N-chloroacetyl, N-dichloroacetyl, N-trichloroacetyl, N-trifluoroacetyl, N-o-nitrophenylacetyl, N-o-nitrophenoxyacetyl, N-acetoacetyl, N-acetylpyridinium, N-3-phenylpropionyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-isobutyryl, N-o-nitrocinnamoyl, N-picolinoyl, N-(N'-acetylmethionyl), N-(N'-benzoylphenylalanyl), N-benzoyl, N-p-phenylbenzoyl, N-p-methoxybenzoyl, N-o-nitrobenzoyl or N-o-(benzoyloxymethyl)benzoyl amide groups);

(c) alkyl groups (e.g. N-allyl, N-phenacyl, N-3-acetoxypropyl, N-(4-nitro-1-cyclohexyl-2-oxo-pyrrolin-3-yl), N-methoxymethyl, N-chloroethoxymethyl, N-benzyloxymethyl, N-pivaloyloxymethyl, N-2-tetrahydropyranyl, N-2,4-dinitrophenyl, N-benzyl, N-3,4-dimethoxybenzyl, N-o-nitrobenzyl, N-di(p-methoxyphenyl)methyl, N-triphenylmethyl, N-(p-methoxyphenyl) diphenylmethyl, N-diphenyl-4-pyridylmethyl, N-2-picolyl N'-oxide or N-dibenzosuberyl groups);

(d) phosphinyl and phosphoryl groups (e.g. N-diphenylphosphinyl, N-dimethylthiophosphinyl, N-diphenylthiophosphinyl, N-diethylphosphoryl, N-dibenzylphosphoryl or N-phenylphosphoryl groups);

(e) sulfenyl groups (e.g. N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl or N-triphenylmethylsulfenyl groups);

(f) sulfonyl groups (e.g. N-benzenesulfonyl, N-p-methoxybenzenesulfonyl, N-2,4,6-trimethylbenzenesulfonyl, N-toluenesulfonyl, N-benzylsulfonyl, N-p-methylbenzylsulfonyl, N-trifluoromethylsulfonyl or N-phenacylsulfonyl); and (g) the N-trimethylsilyl group.

Compounds of formulae I and IA in which the fragment

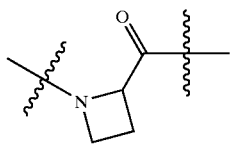

is in the S-configuration are preferred. Compounds of formulae I and IA in which the fragment

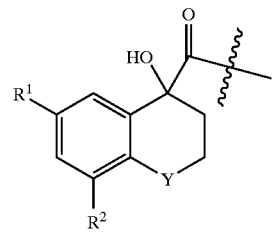

is in the R-configuration are preferred.

The wavy lines on the bonds in the above two fragments signify the bond positions of the fragments.

Compounds of formula IA may be prepared directly from compounds of formula I, in an analogous manner to compounds of formula I, or using procedures appropriately adapted from those used to prepare compounds of formula I. In this respect, processes that may be used to prepare compounds of formula IA include:

(1) for compounds of formula IA in which one of $D^1$ and $D^2$ represents —$OR^7$ (in which $R^7$ represents H, $C_{6-10}$ aryl, $C_{1-10}$ alkyl (which latter group is optionally substituted by one or more halo groups) or $C_{1-3}$ alkylphenyl), reaction of a compound of formula XIV,

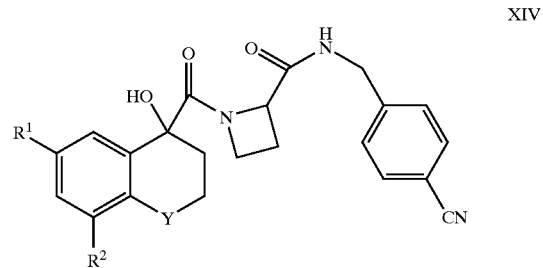

XIV wherein Y, $R^1$ and $R^2$ are as hereinbefore defined, with a compound of formula XV, $H_2NOR^a$  XV wherein $R^a$ represents H, $C_{6-10}$ aryl, $C_{1-10}$ alkyl (which latter group is optionally substituted by one or more halo groups) or $C_{1-3}$ alkylphenyl, for example at between 40 and 60° C., in the presence of a suitable base (e.g. TEA) and an appropriate organic solvent (e.g. THF, $CH_3CN$, DMF or DMSO), optionally by pre-treating the compound of formula XIV with gaseous HCl, in the presence of a lower alkyl (e.g. $C_{1-6}$ alkyl) alcohol (e.g. ethanol) at, for example, 0° C., to form a compound of formula XVI,

XVI

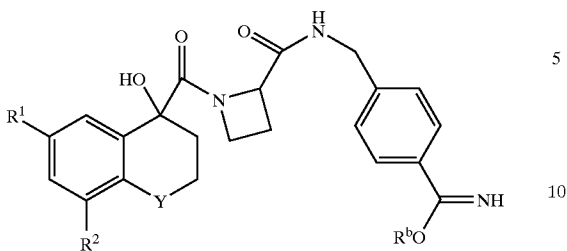

wherein $R^b$ represents lower (e.g. $C_{1-6}$) alkyl, such as ethyl, and Y, $R^1$ and $R^2$ are as hereinbefore defined, which compound may be isolated if desired;

(2) for compounds of formula IA in which one of $D^1$ and $D^2$ represents —$OR^7$ (in which $R^7$ represents H, $C_{6-10}$ aryl, $C_{1-10}$ alkyl (which latter group is optionally substituted by one or more halo groups) or $C_{1-3}$ alkylphenyl), reaction of a corresponding compound of formula IA, in which one of $D^1$ and $D^2$ represents —$C(O)OR^{12}$ (e.g. —$C(O)O$—$CH_2CH_2$—$Si(CH_3)_3$) and the other represents H, with a compound of formula XV, as hereinbefore defined, for example at between room and reflux temperature in the presence of an appropriate organic solvent (e.g. THF, $CH_3CN$, DMF or DMSO), followed by removal of the —$C(O)OR^{12}$ group under conditions known to those skilled in the art;

(3) for compounds of formula IA in which $D^1$ or $D^2$ represents $R^8$, reaction of a corresponding compound of formula I or a corresponding compound of formula IA in which $D^1$ or $D^2$ (as appropriate) represents H with a compound of formula XVII, $L^3$—$R^8$  XVII wherein $L^3$ represents a leaving group, such as halo or p-nitrophenoxy, and $R^8$ is as hereinbefore defined, for example at between 0° C. and room temperature in the presence of a suitable base (e.g. NaOH) and an appropriate organic solvent (e.g. THF) and/or water;

(4) for compounds of formula IA in which one of $D^1$ and $D^2$ represents —$OR^7$ (wherein $R^7$ does not represent H), reaction of a corresponding compound of formula IA in which one of $D^1$ and $D^2$ represents —OH with a compound of formula XVIII, $L^3$—$R^{7a}$  XVIII wherein $R^{7a}$ represents $R^7$ as hereinbefore defined, except that it does not represent H, and $L^3$ is as hereinbefore defined, for example at between 0° C. and reflux temperature, optionally in the presence of an appropriate solvent (e.g. DCM, THF, MeCN or DMF) and a suitable base (e.g. $Et_3N$ or pyridine); or (5) for compounds of formula IA in which one of $D^1$ and $D^2$ represents H and the other represents —$C(R^{9a})(R^{9b})$ $R^{10}$, wherein $R^{10}$ represents —$OC(O)R^{16a}$, —$OC(O)$ $OR^{17}$ or —$OC(O)N(R^{18b})R^{17}$, reaction of a corresponding compound of formula XIX,

XIX

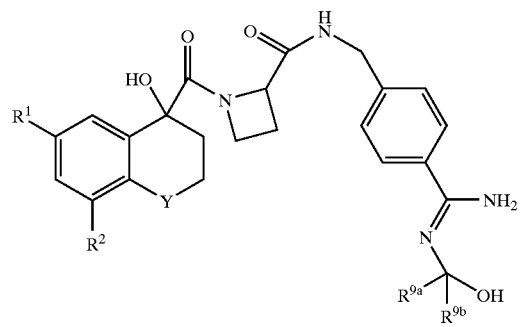

wherein Y, $R^1$, $R^2$, $R^{9a}$ and $R^{9b}$ are as hereinbefore defined with a compound of formula XX, $L^3$—$C(O)R^c$  XX wherein $R^c$ represents $R^{16a}$, —$OR^{17}$ or —$N(R^{18b})R^{17}$, and $L^3$, $R^6$, $R^{17}$ and $R^{18b}$ are as hereinbefore defined, for example under conditions described hereinbefore (e.g. as in step (4) above).

Compounds of formula XIV may be prepared in an analogous fashion to compounds of formula I, for example by the coupling of p-cyano-benzylamine with a compound of formula IV, as hereinbefore defined, under conditions such as those described hereinbefore for the synthesis of compounds of formula I (see, for example, process steps (i) and (ii)).

Compounds of formula XIX may be prepared by reaction of a corresponding compound of formula I with an excess of a compound of formula XXI, $R^{9a}C(O)R^{9b}$  XXI wherein $R^{9a}$ and $R^{9b}$ are as hereinbefore defined, for example under conditions known to those skilled in the art.

Compounds of formula IA in which $D^1$, $D^2$ and $R^3$, together with the amidine group to which they are attached, represent a group IIa may be prepared by reaction of a corresponding compound of formula IA in which $D^1$ represents OH with a compound of formula XXII, HalC(O)CH($R^4$)Hal  XXII wherein Hal represents halo (e.g. chloro) and $R^4$ is as hereinbefore defined, for example at room temperature in the presence of a suitable base (e.g. triethylamine) and an appropriate organic solvent (e.g. dichloromethane), followed by cyclisation of the resultant intermediate, for example by refluxing in the presence of an appropriate base (e.g. sodium hydride) in a suitable organic solvent (e.g. THF).

Compounds of formula IA in which $D^1$, $D^2$ and $R^3$, together with the amidine group to which they are attached, represent a group IIb may be prepared by reaction of a corresponding compound of formula XXIII,

XXIII

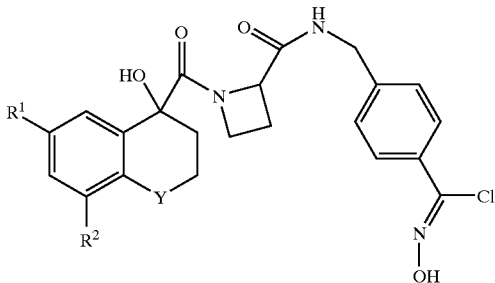

wherein Y, R¹ and R² are as hereinbefore defined with a compound of formula XXIV,

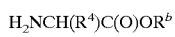
H₂NCH(R⁴)C(O)OR^b    XXIV wherein $R^b$ and $R^4$ are as hereinbefore defined, for example at room temperature in the presence of a suitable base (e.g. triethylamine) and an appropriate organic solvent (e.g. ethanol).

Compounds of formula IA in which $D^1$, $D^2$ and $R^3$, together with the amidine group to which they are attached, represent a group IIc may be prepared by reaction of a corresponding compound of formula IA in which $D^1$ represents OH with a compound of formula XXV,

R⁴CHO    XXV wherein $R^4$ is as hereinbefore defined, for example at room temperature, followed by oxidation of the resultant intermediate under conditions known to those skilled in the art.

Compounds of formula IA in which $D^1$, $D^2$ and $R^3$, together with the amidine group to which they are attached, represent a group IId may be prepared by cyclisation of a compound of formula XXVI,

XXVI

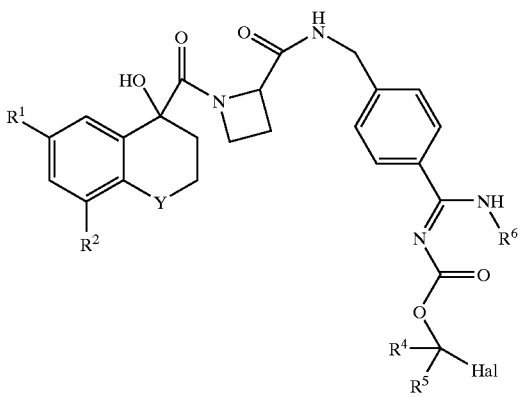

wherein Hal is as hereinbefore defined (especially iodo) and Y, R¹, R² R⁴, R⁵ and R⁶ are as hereinbefore defined, for example at room temperature in the presence of a suitable base (e.g. DIPEA) and an appropriate solvent (e.g. dichloromethane).

Compounds of formula XXVI may be prepared by reaction of a compound of formula XXVII,

XXVII

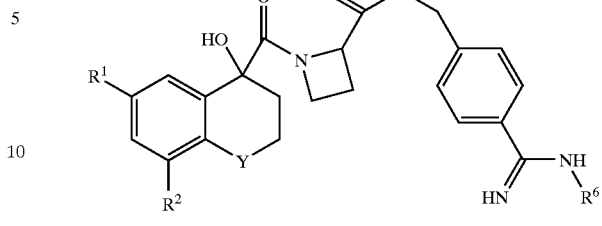

wherein Y, R¹, R² and R⁶ are as hereinbefore defined with a compound of formula XXVIII,

Hal—C(O)OC(R⁴)(R⁵)Hal    XXVIII wherein Hal, R⁴ and R¹ are as hereinbefore defined for example at room temperature in the presence of a suitable base (e.g. triethylamine) and an appropriate organic solvent (e.g. dichloromethane). It is preferred that, in compounds of formula XXVIII, Hal represents chloro. In such cases, the intermediate of formula XXVI that is formed comprises a chloro group, which, before cyclisation, is preferably converted to an iodo group, using techniques well know to those skilled in the art (e.g. reaction with NaI).

Compounds of formula IA in which $D^1$, $D^2$ and $R^3$, together with the amidine group to which they are attached, represent a group IIe may be prepared by reaction of a corresponding compound of formula XXIX,

XXIX

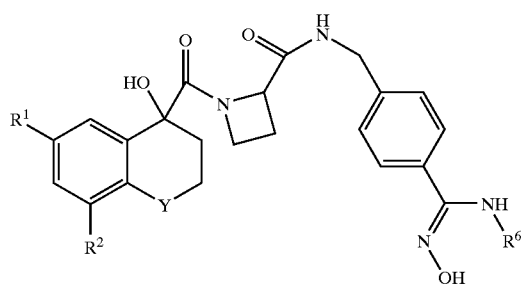

wherein Y, R¹, R² and R⁶ are as hereinbefore defined with formaldehyde in water, for example at reflux temperature.

Compounds of formulae XV, XVII, XVIII, XX, XXI, XXII, XXIII, XXIV, XXV, XXVII, XXVIII and XXIX and derivatives thereof, are either commercially available, are known in the literature, or may be obtained either by analogy with the processes described herein, or by conventional synthetic procedures, in accordance with standard techniques, from readily available starting materials using appropriate reagents and reaction conditions (e.g. as described hereinafter).

Compounds of formula IA may be isolated from their reaction mixtures using conventional techniques.

Substituents on the aromatic and/or non-aromatic, carbocyclic and heterocyclic ring(s) in compounds of formulae IA, XIV, XV, XVI, XVII, XVIII, XIX, XX, XXI, XXIII, XXVI, XXVIII and XXIX may be introduced and/or interconverted using techniques well known to those skilled in the art. For example, hydroxy may be alkylated to give alkoxy or acylated to give acyloxy, and alkoxy and acyloxy may be hydrolysed to give hydroxy.

It will be appreciated by those skilled in the art that in the processes described above (in relation to compounds of formulae I and IA) the functional groups of intermediate compounds may need to be protected by protecting groups.

Functional groups that it is desirable to protect include hydroxy, amino, aldehyde, ketone, 2-hydroxycarboxylic acid and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino and amidino include t-butyloxycarbonyl, benzyloxycarbonyl or 2-trimethylsilylethoxycarbonyl (Teoc). Amidino nitrogens may also be protected by hydroxy or alkoxy groups, and may be either mono- or diprotected. Aldehydes and ketones may be protected as acetals and ketals, respectively, by reacting with e.g. ethylene glycol. 2-Hydroxy carboxylic acids may be protected by condensing with e.g. acetone.

The protection and deprotection of functional groups may take place before or after coupling, or before or after any other reaction in the abovementioned schemes.

Protecting groups may be removed in accordance with techniques that are well known to those skilled in the art and as described hereinafter. Persons skilled in the art will appreciate that, in order to obtain compounds of formula I, or formula IA, in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

For example, this is particularly true in respect of the synthesis of compounds of formula IA. In this case, $D^1$ or $D^2$ groups which do not represent H may be introduced at an earlier stage in the overall synthesis using the process steps described hereinbefore (see, for example, steps (1) to (5) above). Further, in the synthesis of compounds of formula I, the —OH group that is in the α-position relative to the carboxylic acid in compounds of formulae III and IV may need to be protected prior to the coupling steps described above.

Accordingly, the order and type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", $3^{rd}$ edition, T W Greene & P G M Wutz, Wiley-Interscience (1999).

Protected derivatives of compounds of formulae I and IA may be converted chemically to compounds of formulae I and IA using standard deprotection techniques (e.g. hydrogenation).

Medical and Pharmaceutical Use

Compounds of the invention may possess pharmacological activity as such. Compounds of the invention that may possess such activity include, but are not limited to, compounds of formula I.

However, other compounds of the invention (including compounds of formula IA) may not possess such activity, but may be administered parenterally or orally, and thereafter metabolised in the body to form compounds that are pharmacologically active (including, but not limited to, corresponding compounds of formula I). Such compounds (which also includes compounds that may possess some pharmacological activity, but that activity is appreciably lower than that of the "active" compounds to which they are metabolised), may therefore be described as "prodrugs" of the active compounds.

Thus, the compounds of the invention are useful because they possess pharmacological activity, and/or are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, compounds of the invention are potent inhibitors of thrombin either as such and/or (e.g. in the case of prodrugs), are metabolised following administration to form potent inhibitors of thrombin, for example as demonstrated in the tests described below.

By "prodrug of a thrombin inhibitor", we include compounds that form a thrombin inhibitor, in an experimentally-detectable amount, and within a predetermined time (e.g. about 1 hour), following oral or parenteral administration.

The compounds of the invention are thus expected to be useful in those conditions where inhibition of thrombin is required.

The compounds of the invention are thus indicated in the treatment and/or prophylaxis of thrombosis and hypercoagulability in blood and tissues of animals including man.

It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S or heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction or caused by congestive heart failure.

Moreover, the compounds of the invention are expected to have utility in prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of the invention to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutically acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors, ADP-receptor ($P_2T$) antagonists and inhibitors of carboxypeptidase U (CPU).

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutic treatment of humans are about 0.001–100 mg/kg body weight at peroral administration and 0.001–50 mg/kg body weight at parenteral administration.

The compounds of the invention have the advantage that they may, or may be metabolised to compounds that may, be more efficacious, be less toxic, be longer acting, have a broader range of activity, be more potent, produce fewer side effects, be more easily absorbed, or have a better pharmacokinetic profile, than, or have other useful pharmacological, physical, or chemical, properties over, compounds known in the prior art.

Biological Tests

The following test procedures may be employed.

Test A

Determination of Thrombin Clotting Time (TT)

The inhibitor solution (25 ⌧L) is incubated with plasma (25 ⌧L) for three minutes. Human thrombin (T 6769; Sigma Chem. Co or Hematologic Technologies) in buffer solution, pH 7.4 (25 ⌧L, 4.0 NIH units/mL), is then added and the clotting time measured in an automatic device (KC 10; Amelung).

The thrombin clotting time (TT) is expressed as absolute values (seconds) as well as the ratio of TT without inhibitor ($TT_0$) to TT with inhibitor ($TT_i$). The latter ratios (range 1–0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK).

Test B

Determination of Thrombin Inhibition With a Chromogenic, Robotic Assay

The thrombin inhibitor potency is measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 ⌧L), 0.1–1 mmol/L, are diluted serially 1:3 (24+48 ⌧L) with DMSO to obtain ten different concentrations, which are analysed as samples in the assay. 2 ⌧L of test sample is diluted with 124 ⌧L assay buffer, 12 ⌧L of chromogenic substrate solution (S-2366, Chromogenix, Mölndal, Sweden) in assay buffer and finally 12 ⌧L of ꞵ-thrombin solution (Human (α-thrombin, Sigma Chemical Co. or Hematologic Technologies) in assay buffer, are added, and the samples mixed. The final assay concentrations are: test substance 0.00068–13.3 ⌧mol/L, S-2366 0.30 mmol/L, ꞵ-thrombin 0.020 NIHU/mL. The linear absorbance increment during 40 minutes incubation at 37° C. is used for calculation of percentage inhibition for the test samples, as compared to blanks without inhibitor. The $IC_{50}$-robotic value, corresponding to the inhibitor concentration which causes 50% inhibition of the thrombin activity, is calculated from a log concentration vs. % inhibition curve.

Test C

Determination of the Inhibition Constant $K_i$ for Human Thrombin $K_i$-determinations are made using a chromogenic substrate method, performed at 37° C. on a Cobas Bio centrifugal analyser (Roche, Basel, Switzerland). Residual enzyme activity after incubation of human ꞵ-thrombin with various concentrations of test compound is determined at three different substrate concentrations, and is measured as the change in optical absorbance at 405 nm.

Test compound solutions (100 μL; normally in buffer or saline containing BSA 10 g/L) are mixed with 200 μL of human ƒ-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, is added to 320 μL of the substrate S-2238 (Chromogenix AB, Mölndal, Sweden) in assay buffer, and the absorbance change (mA/min) is monitored. The final concentrations of S-2238 are 16, 24 and 50 μmol/L and of thrombin 0.125 NIH U/mL.

The steady state reaction rate is used to construct Dixon plots, i.e. diagrams of inhibitor concentration vs. 1/(mA/min). For reversible, competitive inhibitors, the data points for the different substrate concentrations typically form straight lines which intercept at $x=-K_i$.

Test D

Determination of Activated Partial Thromboplastin Time (APTT)

APTT is determined in pooled normal human citrated plasma with the reagent PTT Automated 5 manufactured by Stago. The inhibitors are added to the plasma (10 μL inhibitor solution to 90 μL plasma) and incubated with the APTT reagent for 3 minutes followed by the addition of 100 μL of calcium chloride solution (0.025 M) and APTT is determined by use of the coagulation analyser KC10 (Amelung) according to the instructions of the reagent producer.

The clotting time is expressed as absolute values (seconds) as well as the ratio of APTT without inhibitor ($APTT_0$) to APTT with inhibitor ($APTT_1$). The latter ratios (range 1–0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK). $IC_{50}APTT$ is defined as the concentration of inhibitor in human plasma that doubled the Activated Partial Thromboplastin Time.

Test E

Determination of Thrombin Time ex vivo

The inhibition of thrombin after oral or parenteral administration of the compounds of formula I, dissolved in ethanol:Solutol3:water (5:5:90), is examined in conscious rats which, one or two days prior to the experiment, are equipped with a catheter for blood sampling from the carotid artery. On the experimental day blood samples are withdrawn at fixed times after the administration of the compound into plastic tubes containing 1 part sodium citrate solution (0.13 mol per L) and 9 parts of blood. The tubes are centrifuged to obtain platelet poor plasma. The plasma is used for determination of thrombin time or ecarin clotting time (ECT) as described below.

The citrated rat plasma, 100 μL, is diluted with a saline solution, 0.9%, 100 μL, and plasma coagulation is started by the addition of human thrombin (T 6769, Sigma Chem Co, USA or Hematologic Technologies) in a buffer solution, pH 7.4, 100 μL, or ecarin (Pentapharm). The clotting time is measured in an automatic device (KC 10, Amelung, Germany).

Where a "prodrug" compound of formula I (e.g. of formula IA) is administered, concentrations of the appropriate active thrombin inhibitor of formula I in the rat plasma are estimated by the use of standard curves relating the thrombin time or ecarin clotting time in the pooled citrated rat plasma to known concentrations of the corresponding "active" thrombin inhibitor dissolved in saline.

Based on the estimated plasma concentrations of the active thrombin inhibitor (which assumes that thrombin time or ECT prolongation is caused by the aforementioned compound) in the rat, the area under the curve after oral and/or parenteral administration of the corresponding prodrug compound of formula I is calculated (AUCpd) using the trapezoidal rule and extrapolation of data to infinity.

The bioavailability of the active thrombin inhibitor after oral or parenteral administration of the prodrug is calculated as below:

[(AUCpd/dose)/(AUCactive,parenteral/dose]×100 where AUCactive,parenteral represents the AUC obtained after parenteral administration of the corresponding active thrombin inhibitor to conscious rats as described above.

Test F

Determination of Thrombin Time in Urine ex vivo

The amount of the "active" thrombin inhibitor that is excreted in urine after oral or parenteral administration of "prodrug" compounds of the invention, dissolved in ethanol:Solutol3:water (5:5:90), is estimated by determination of the thrombin time in urine ex vivo (assuming that thrombin time prolongation is caused by the aforementioned compound). Conscious rats are placed in metabolism cages, allowing separate collection of urine and faeces, for 24 hours following oral administration of compounds of the invention. The thrombin time is determined on the collected urine as described below.

Pooled normal citrated human plasma (100 μL) is incubated with the concentrated rat urine, or saline dilutions thereof, for one minute. Plasma coagulation is then initiated by the administration of human thrombin (T 6769, Sigma Chem Company) in buffer solution (pH 7.4; 100 μL). The clotting time is measured in an automatic device (KC 10; Amelung).

The concentrations of the active thrombin inhibitor in the rat urine are estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) can be calculated.

The bioavailability of the active thrombin inhibitor after oral or parenteral administration of the prodrug is calculated as below:

[(AMOUNTpd/dose)/(AMOUNTactive,parenteral/dose]×100 where AMOUNTactive,parenteral represents the amount excreted in the urine after parenteral administration of the corresponding active thrombin inhibitor to conscious rats as described above.

Test G

Metabolic Activation of Prodrug Compounds in vitro

Prodrug compounds of formula IA are incubated at 37° C. with liver microsomes or 10 000 g (referring to the centrifuge speed) supernatant fractions (i.e. s9 fraction) prepared from human or rat liver homogenate. The total protein concentration in the incubations are 1 or 3 mg/mL dissolved in 0.05 mol/L TRIS buffer (pH 7.4), and with the cofactors NADH (2.5 mmol/L) and NADPH (0. 8 mmol/L) present. The total volume of the incubate is 1.2 mL. The initial prodrug concentrations are 5 or 10 ⊠mol/L. Samples are collected from the incubate at regular is intervals more than 60 minutes after the start of the incubations. Samples (25 ⊠L) from the incubate are mixed with an equal volume of human or rat plasma and an appropriate amount of thrombin, and the clotting time (i.e. thrombin time) is measured on a coagulometer (KC 10; Amelung). The amount of "active" thrombin inhibitor formed is estimated by the use of standard curves relating the thrombin time in pooled citrated human or rat plasma to known concentrations of the corresponding "active thrombin inhibitor".

The amount of "active" thrombin inhibitor is alternatively, or in addition to the above-mentioned method, estimated by the use of LC-MS.

Test H

Determination of Plasma Clearance in Rat

Plasma clearance was estimated in male Sprague Dawley rats. The compound was dissolved in water and administered as a subcutaneous bolus injection at a dose of 4 µmol/kg. Blood samples were collected at frequent intervals up to 5 hours after drug administration. Blood samples were centrifuged and plasma was separated from the blood cells and transferred to vials containing citrate (10% final concentration). The ecarin clotting time (ECT) was then determined in each plasma sample by the use of a coagulometer (KC10; Amelung). The plasma concentration in each sample was determined by the use of a standard curve relating the ECT in pooled citrated plasma samples to known concentrations of the compound. The area under the plasma concentration-time profile was estimated using the log/linear trapezoidal rule and extrapolated to infinite time. Plasma clearance (CL) of the compound was then determined as $$CL = Dose/AUC$$

The values are reported in mL/min/kg.

Test I

Determination of in vitro Stability of Active Thrombin Inhibitors

Liver microsomes were prepared from Sprague-Dawley rats and human liver samples according to internal SOPs. The compounds were incubated at 37° C. at a total microsome protein concentration of 3 mg/mL in a 0.05 mol/L TRIS buffer at pH 7.4, in the presence of the cofactors NADH (2.5 mmol/L) and NADPH (0.8 mmol/L). The initial concentration of compound was 5 or 10 µmol/L. Samples were taken for analysis up to 60 minutes after the start of the incubation. The enzymatic activity in the collected sample was immediately stopped by adding 20% myristic acid at a volume corresponding to 3.3% of the total sample volume. The concentration of compound remaining (FINAL CONC) in the 60 min. sample was determined by means of LCMS using a sample collected at zero time as reference (START CONC). The % of degraded thrombin inhibitor was calculated as:

$$100\% \times \frac{[\text{START CONC}] - [\text{FINAL CONC}]}{[\text{START CONC}]}$$

Test J

Arterial Thrombosis Model

Vessel damage was induced by applying ferric chloride ($FeCl_3$) topically to the carotid artery. Rats are anaesthetised with an intraperitoneal injection of sodium pentobarbital (80 mg/kg; Apoteksbolaget; Umea, Sweden), followed by continuous infusion (12 mg/kg/h) throughout the experiment. Rat body temperature was maintained at 38° C. throughout the experiment by external heating. The experiment started with a 5 minutes control period. Five minutes later, human $^{125}I$-fibrinogen (80 kBq; IM53; Amersham International, Buckinghamshire, UK) was given intravenously and was used as a marker for the subsequent incorporation of fibrin (ogen) into the thrombus. The proximal end of the carotid artery segment was placed in a plastic tube (6 mm; Silastic®; Dow Corning, Mich., USA) opened lengthways, containing $FeCl_3$-soaked (2 µl; 55% w/w; Merck, Darmstadt, Germany) filter paper (diameter 3 mm; IF; Munktell, Grycksbo, Sweden). The left carotid artery was exposed to $FeCl_3$ for 10 minutes and was then removed from the plastic tube and soaked in saline. Fifty minutes later, the carotid artery was removed and rinsed in saline. Reference blood samples were also taken for determination of blood $^{125}I$-activity, 10 minutes after the injection of 125I -fibrinogen, and at the end of the experiment. The $^{125}I$-activity in the reference blood samples and the vessel segment were measured in a gamma counter (1282 Compugamma; LKB Wallac Oy, Turku, Finland) on the same day as the experiment was performed. The thrombus size was determined as the amount of $^{125}I$-activity incorporated in the vessel segment in relation to the $^{125}I$-activity in the blood (cpm/mg).

EXAMPLES

The invention is illustrated by way of the following examples. The amino acid Aze is defined as the S-isomer if not otherwise specified. The examples were obtained as diastereoisomers if not otherwise specified.

Example 1

(R)-6-Chloro-4-hydroxy-8-methoxy-1,1-dioxothiochromane-4-yl-C(O)-Aze-Pab (i) 3-(4-Chloro-2-methoxyphenylthio)propanoic Acid, Ethyl Ester 4-Chloro-2-methoxythiophenol (5.78 g, 33 mmol), triethylamine (5.0 mL, 36 mmol) and ethyl 3-bromopropanoate (4.6 mL, 36 mmol) were dissolved in ethyl acetate (50 mL) and refluxed for 2 h. Water was added and the liquid phases were separated. The aqueous phase was extracted two times with ethyl acetate. The combined organic fractions were washed with 1 M aq. HCl and then concentrated in vacuo. Purification by flash chromatography ($SiO_2$; heptane: dichloromethane (1:1, 0:1)) afforded the sub-title compound as a yellow solid. Yield: 3.0 g (30%). Estimated purity: 75% (NMR).

Bis(4-chloro-2-methoxyphenyl) disulfide (1.7 g, 4.9 mmol) was also isolated (vide supra). This material was dissolved in THF:EtOH (80 mL of 1:1) and stirred under $N_2(g)$. A solution of sodium borohydride (0.38 g, 10 mmol) in 2 M aq. NaOH (2 mL) and water (10 mL) was added. The yellow colour disappeared. After 1 h at room temperature ethyl 3-bromopropanoate (1.3 mL, 10 mmol) was added, resulting in evolution of gas and a white precipitate. After stirring overnight, the solvent was removed in vacuo and the residue transferred to a separatory funnel with water and dichloromethane. The organic phase was dried (MgSO$_4$) and concentrated in vacuo affording an additional 2.36 g (88%) of the sub-title compound, a yellow oil that solidified after a few hours. $^1$H NMR (400 MHz; CDCl$_3$): δ 7.29 (d, 1H), 6.94 (dd, 1H), 6.87 (d, 1H), 4.17 (q, 2H), 3.92 (s, 3H), 3.15 (t, 2H), 2.61 (t, 2H), 1.18 (t, 3H).

(ii) 3-(4-Chloro-2-methoxyphenylthio)propanoic Acid

To an ice/water-cooled solution of 3-(4-chloro-2-methoxyphenylthio)-propanoic acid, ethyl ester (2.31 g, 8.41 mmol; see step (i) above) in THF (50 mL) was added a solution of lithium hydroxide monohydrate (0.43 g, 10 mmol) in water (25 mL). The temperature was allowed to slowly rise to ambient overnight. THF was removed in vacuo, the residue was washed with diethyl ether, acidified with 2 M aq. HCl and then extracted with diethyl ether. The combined ether fractions were extracted with sat. aq. sodium hydrogencarbonate. Careful acidification with aq. HCl afforded a precipitate that was filtered off and air-dried.

Yield: 1.71 g (82%). MS(m/z) 245 (M−1)$^−$.

(iii) 6-Chloro-8-methoxy-4-thiochromanone

To a solution/suspension of 3-(4-chloro-2-methoxyphenylthio)propanoic acid (1.46 g, 5.92 mmol; see step (ii) above) in dichloromethane (50 mL) under N$_2$(g) was added boron trifluoride dimethyl etherate (1.4 mL, 15 mmol) and trifluoroacetic anhydride (2.1 mL, 15 mmol). After 2.5 h at rt the reaction was quenched with water (2 mL), then washed with more water. The deep green colour disappeared when it was further washed with sat. aq. sodium hydrogencarbonate. Drying (MgSO$_4$) and removal of the solvent in vacuo afforded the sub-title compound as a yellow solid.

Yield: 1.19g(88%) $^1$H NMR (300 MHz; CDCl$_3$) δ 7.73 (d, 1H), 6.92 (d, 1H), 3.91 (s, 3H), 3.21 (m, 2H), 2.95 (m, 2H).

(iv) 6-Chloro-4-hydroxy-8-methoxythiochromane-4-yl-carboxylic Acid, Ethyl Ester

To a stirred solution/suspension of 6-chloro-8-methoxy-4-thiochromanone (2.24 g; 9.79 mmol; see step (iii) above) and zinc iodide (0.078 g; 0.24 mmol) in dry methylene chloride (20 mL) under N$_2$(g) was added trimethylsilyl cyanide (1.35 mL; 10.1 mmol). After 2 days at room temperature, the reaction mixture was slowly added to stirred ice/water-cooled absolute ethanol (50 mL), presaturated with HCl(g) at 0° C. After this addition, the cooling bath was removed and the reaction was monitored using reversed-phase HPLC. After 2 h at rt, the solvents were removed in vacuo. The residue was dissolved in THF (40 mL) and H$_2$SO$_4$ (aq.; 0.5 M; 40 mL) and stirred overnight. After concentration under reduced pressure (THF removed), extraction with EtOAc and removal of the solvents in vacuo, 3.7 g of crude oil was obtained. Purification using preparative reversed-phase HPLC (acetonitrile:0.1 M aq. ammonium acetate) afforded, after extraction of the appropriate fractions with methylene chloride, the sub-title compound as an oil that slowly crystallized.

Yield: 2.26 g (76%) $^1$H NMR (300 MHz; CDCl$_3$) δ 6.80 (d, 1H), 6.73 (d, 1H), 4.20–4.35 (m, 2H), 3.98 (s, 1H), 3.87 (s, 3H), 3.19 (m, 1H), 2.98 (m, 1H), 2.27–2.42 (m, 2H), 1.23 (t, 3H).

(v) 6-Chloro-4-hydroxy-8-methoxythiochromane-4-yl-carboxylic Acid

To an ice/water-cooled solution of 6-chloro-4-hydroxy-8-methoxythiochromane-4-yl-carboxylic acid, ethyl ester (2.26 g, 7.46 mmol; see step (iv) above) in THF (20 mL) was added a solution of lithium hydroxide monohydrate (0.68 g, 16 mmol) in water (10 mL). The temperature was allowed to slowly rise to ambient overnight. THF was removed in vacuo, the residue was washed with diethyl ether, acidified with 2 M aq. HCl and then extracted with ethyl acetate. Drying (MgSO$_4$) and removal of the solvent in vacuo afforded the sub-title compound.

Yield: 1.53 g (75%). MS(m/z) 273 (M−1)$^−$.

(vi) (R)-6-Chloro-4-hydroxy-8-methoxythiochromane-4-yl-carboxylic Acid

The enantiomers of 6-chloro-4-hydroxy-8-methoxythiochromane-4-yl-carboxylic acid (3.00 g, 10.9 mmol; see step (v) above) were separated using chiral chromatography (Kromasil TBB; heptane:ethyl acetate:formnic acid) affording 1.13 g of the faster moving, not wanted S-enantiomer, and 1.19 g (79%) of the slower moving sub-title compound. ee=94.6%

$^1$H NMR (500 MHz; CD$_3$OD) δ 6.97 (d, 1H), 6.83 (d, 1H), 3.83 (s, 3H), 3.07 (m, 1H), 2.98 (m, 1H), 2.40 (m, 1H), 2.27 (m, 1H).

(vii) (R)-6-Chloro-4-hydroxy-8-methoxy-1,1-dioxothiochromane-4-yl-carboxylic Acid A solution of (R)-6-chloro-4-hydroxy-8-methoxythiochromane-4-yl-carboxylic acid (0.55 g, 2.0 mmol; from step (vi) above) and aqueous hydrogen peroxide (1.0 mL of 35%, 10 mmol) in acetic acid (20 mL) was stirred overnight at ambient temperature. The solvent was removed in vacuo, after which the residue was dissolved in water and then freeze dried. Yield: 0.63 g (100%).

MS(m/z) 305 (M−1)$^−$. $^1$H NMR (400 MHz; CD$_3$OD) δ 7.23 (d, 1H), 7.06 (d, 1H), 3.96 (s, 3H), 3.61 (m, 2H), 2.85 (m, 1H), 2.53 (m, 1H).

(viii) (R)-6-Chloro-4-hydroxy-8-methoxy-1,1-dioxothiochromane-4-yl-C(O)-Aze-Pab(Teoc)

HATU (0.94 g; 2.5 mmol) was added to a solution of (R)-6-chloro-4-hydroxy-8-methoxy-1,1-dioxothiochromane-4-yl-carboxylic acid (0.63 g; 2.05 mmol; see step (vii) above) in DMF (10 mL) at 0° C. After 1 h, a solution of H-Aze-Pab(Teoc)x2 HCl (1.1 g; 2.5 mmol; see international patent application WO 98/57932) and N,N-diisopropylethylamine (1.4 mL; 8.0 mmol) in DMF (5 mL) was added dropwise. The temperature was allowed slowly to rise to ambient overnight. The solvents were removed in vacuo and the residue was purified using reversed-phase HPLC (acetonitrile:0.1 M aq. ammonium acetate). Freeze drying of the appropriate fractions afforded the sub-title compound as a colourless solid.

Yield: 0.50 g (37%) MS(m/z) 663 (M−1)$^−$; 665 (M +1)$^+$.

(An alternative method of obtaining (R)-6-chloro-4-hydroxy-8-methoxy-1,1-dioxothiochromane-4-yl-C(O)-Aze-Pab(Teoc) is as follows: HATU (0.47 g, 1.2 mmol) was added to a solution of (R)-6-chloro-4-hydroxy-8-methoxythiochromane-4-yl-carboxylic acid (0.31 g, 1.1 mmol; see step (vi) above) in DMF (7 mL) at 0° C. After 1 h, a solution of H-Aze-Pab(Teoc)x2HCl (0.61 g, 1.4 mmol; prepared as described in international patent application WO 98/57932) and 2,4,6-collidine (0.67 mL, 5.1 mmol) in DMF (9 mL) was added dropwise. After 2 h the reaction mixture was put in a freezer overnight. The solvent was removed in vacuo, the residue dissolved in ethyl acetate and then washed with aq. sat. sodium hydrogencarbonate. Purification using reversed-phase HPLC (acetonitrile: 0.1 M aq. ammonium acetate) afforded, after freeze-drying of the appropriate fractions, the sub-title compound as a colourless solid. To an ice/water-cooled solution of the (R)-6-chloro-4-hydroxy-8-methoxythiochromane-4-yl-C(O)-Aze-Pab (Teoc) so obtained (0.25 g, 0.39 mmol), in dichloromethane (20 mL), was added m-chloroperbenzoic acid (0.25 g of ~60%, 0.86 mmol), dissolved in a small volume of dichloromethane. The reaction mixture stirred for 2.5 h, then washed with sat. aq. sodium hydrogencarbonate, concentrated in vacuo and purified using reversed-phase HPLC (acetonitrile: 0.1 M aq. ammonium acetate). The fractions of interest were concentrated and extracted with ethyl acetate. Drying ($MgSO_4$) and removal of the solvent in vacuo afforded the sub-title compound. Yield: 0.201 g (76%).)

(ix) (R)-6-Chloro-4-hydroxy-8-methoxy-1,1-dioxothiochromane-4-yl-C(O)Aze-PabxHOAc To a solution of (R)-6-chloro-4-hydroxy-8-methoxy-1,1-dioxothiochromane-4-yl—C(O)-Aze-Pab(Teoc) (0.092 g, 0.14 mmol; see step (viii) above) in THF (15 mL) was added tetrabutylammonium fluoride (0.18 mL of 1.0 M, 0.18 mmol). The solution was stirred at 50° C. for 20 h, at 60° C. for 5 h, then left at rt overnight. The solvent was removed in vacuo. The residue was purified using reversed-phase HPLC (acetonitrile: 0.1 M aq. ammonium acetate) affording the title compound as a white solid, after freeze-drying the appropriate fractions.

Yield: 0.044 g (50%). MS(m/z) 519 (M−1)$^{31}$, 521 (M+1)$^+$.

$^1$H NMR (600 MHz; $CD_3OD$): (complex due to diastereomers/rotamers) δ 7.76 (d, 0.9H, rotamer); 7.66 (d, 1.1H, rotamer); 7.54 (d, 0.9H, rotamer); 7.47 (d, 1.1H, rotamer); 7.12–7.25 (several peaks, 2H); 5.54 (dd, 0.45H, rotamer); 4.54–4.65 (several peaks, 1.55H); 4.43–4.51 (several peaks, 1H); 4.30 (m, 0.55H, rotamer); 4.09 (m, 0.45H, rotamer); 3.99 (m, 0.45H, rotamer); 3.92 (m, 0.55H, rotamer); 3.90 (s, 3H); 3.76 (m, 0.45H, rotamer); 3.60 (m, 1.1H, rotamer); 3.40 (m, 0.45H, rotamer); 2.70–2.88 (several peaks, 1.45H); 2.46–2.61 (several peaks, 1.55H); 2.28 (m, 0.55H, rotamer); 2.14 (m, 0.45H, rotamer); 1.90 (s, 3H).

$^{13}$C NMR (75 MHz; $CD_3OD$): (complex due to diastereomers/rotamers, carbonyl and/or amidine carbons) δ 179.8; 174.2; 173.8; 172.9; 168.1.

Example 2

(R)-6,8-Dichloro-4-hydroxy-1,1-dioxothiochromane-4-yl-C(O)-Aze-Pab (i) 3-(2,4-Dichlorophenylthio)propanoic Acid, Ethyl Ester 2,4-Dichlorothiophenol (5.04 g, 28.2 mmol), caesium carbonate (10.1 g, 31 mmol) and ethyl 3-bromopropanoate (4.2 mL, 33 mmol) in acetone (100 mL) were refluxed overnight under $N_2$(g). After filtration and concentration under reduced pressure, the residue was partitioned between dichloromethane and water. After separation, the aqueous phase was extracted once with dichloromethane. Drying and removal of the solvent in vacuo afforded a liquid residue that contained ~30% (HPLC) of unreacted 2,4-dichlorothiophenol. The mixture was refluxed again with caesium carbonate (4.7 g) and ethyl 3-bromopropanoate (2 mL) in acetonitrile (100 mL) under $N_2$(g) for 2 h. After filtration and concentration under reduced pressure, the residue was dissolved in diethyl ether and washed with 2 M aq. sodium hydroxide and water. Drying and removal of the solvent in vacuo afforded the sub-title compound.

15 Yield: 5.85 g (74%). $^1$H NMR (300 MHz; $CDCl_3$): δ 7.39 (d, 1H), 7.25 (d, 1H), 7.18 (dd, 1H), 4.13 (q, 2H), 3.15 (t, 2H), 2.61 (t, 2H), 1.13 (t, 3H).

(ii) 3-(2,4-Dichlorophenylthio)propanoic Acid

The sub-title compound was prepared using the method described in Example 1(ii) above, starting from 3-(2,4-dichlorophenylthio)propanoic acid, ethyl ester (5.8 g, 20.8 mmol; from step (i) above). Yield: 3.43 g (66%).

MS(m/z) 249 (M−1)$^-$.

(iii) 6,8-Dichloro-4-thiochromanone

A deep red colour was immediately observed when 3-(2,4-dichlorophenylthio)propanoic acid (1.20 g, 4.78 mmol; from step (ii) above) was added to conc. sulfuric acid (30 mL). After stirring overnight at ambient temperature the reaction mixture was poured into ice. The red colour disappeared. Extraction with diethyl ether, washing with aq., sat. sodium hydrogencarbonate, drying ($MgSO_4$) and removal of the solvent in vacuo afforded a deep yellow solid.

Yield: 0.93 g (84%). $^1$H NMR (400 MHz; $CDCl_3$) δ 8.01 (d, 1H), 7.47 (d, 1H), 3.23 (m, 2H), 2.96 (m, 2H).

(iv) 6,8-Dichloro-4-hydroxythiochromane-4-yl-carboxylic Acid, Ethyl Ester

The sub-title compound was prepared according to the method of C. F. Bigge et al. in J. Med. Chem., (1993), 36, 1977 using 6,8-dichloro-4-thiochromanone (2.20 g, 9.44 mmol; from step (iii) above). Yield: 2.75 g (95%). $^1$H NMR (500 MHz; $CDCl_3$) δ 7.30(d, 1H), 7.08 (d, 1H), 4.24–4.35 (m, 2H), 3.23 (m, 1H), 3.04 (ddd, 1H), 2.29–2.41 (m, 2H), 1.25 (t, 3H).

(v) 6,8-Dichloro-4-hydroxythiochromane-4-yl-carboxylic Acid

The sub-title compound was prepared using the method described in Example 1(v) above, starting from 6,8-dichloro-4-hydroxychromane-4-yl-carboxylic acid, ethyl ester (2.74 g, 8.92 mmol; from step (iv) above).

Yield: 2.17 g (87%). MS(m/z) 277 (M−1)$^-$. $^1$H NMR (400 MHz; $CDCl_3$) δ 7.34 (d, 1H), 7.21 (d, 1H), 3.21 (m, 1H), 3.12 (ddd, 1H), 2.35–2.50 (m, 2H), 2.13 (s, 1H).

(vi) (R)-6,8-Dichloro-4-hydroxythiochromane-4-yl-carboxylic Acid

The enantiomers of 6,8-dichloro-4-hydroxychromane-4-yl-carboxylic acid (2.17 g, 7.77 mmol; from step (v) above) were separated using chiral chromatography (Kromasil TBB; heptane: ethyl acetate: formic acid) affording 0.74 g of the faster moving, not wanted S-enantiomer, and 0.72 g (66%) of the slower moving sub-title compound. ee=98.4%

(vii) (R)-6,8-Dichloro-4-hydroxythiochromane-4-yl-C(O)-Aze-Pab(Teoc)

The sub-title compound was prepared analogously to the method described in Example 1(viii) above, starting from (R)-6,8-dichloro-4-hydroxychromane-4-yl-carboxylic acid (0.19 g, 0.68 mmol; from step (vi) above) and H-Aze-Pab (Teoc) (0.37 g, 0.82 mmol; prepared as described in international patent application WO 98/57932). Yield: 0.28 g (65%). MS(m/z) 635 (M−1)$^-$, 637 (M+1)$^+$.

(viii) (R)-6,8-Dichloro-4-hydroxy-1,1-dioxothiochromane-4-yl-C(O)-Aze-Pab(Teoc)

The sub-title compound was prepared analogously to the method described in Example 1(viii) (alternative preparation, second step) above, starting from (R)-6,8-dichloro-4-hydroxy-thiochromane-4-yl-C(O)-Aze-Pab (Teoc) (0.100 g, 0.157 mmol; from step (vii) above) and m-chloroperbenzoic acid (0.125 g of 60%; 0.72 mmol). Yield: 0.040 g (38%). MS(m/z) 667 (M−1)$^-$, 669 (M+1)$^+$.

(ix) (R)-6,8-Dichloro-4-hydroxy-1,1-dioxothiochromane-4-yl-C(O)-Aze-PabxCF$_3$COOH Trifluoroacetic acid (1.0 mL) was added to a stirred ice/water-cooled solution of (R)-6 ,8-dichloro-4-hydroxy-1,1-dioxothiochromane-4-yl—C(O)-Aze-Pab(Teoc) (40 mg, 60 μmol; from step (viii) above) in dichloromethane (10 mL). The cooling bath was removed after 30 min. After 1 h at rt, acetonitrile (30 mL) was added and the solvents were carefully removed under reduced pressure. The residue was dissolved in water and then freeze-dried.

Yield: 27 mg (68%). MS(m/z) 525 (M−1)$^-$, 523 (M+1)$^+$.

$^1$H NMR (400 MHz; $CD_3OD$): (complex due to diastereomers/rotamers) δ 8.74 (m, 1H), 7.45–7.80 (several peaks, 6H), 5.53 (dd, 0.4H, rotamer), 4.35–4.88 (several peaks, 3.8H), 4.09 (m, 0.4H, rotamer), 4.00 (m, 0.4H, rotamer), 3.87 (m, 0.4H, rotamer), 3.68 (m, 1.2H, rotamer), 3.45 (ddd, 0.4H); 2.78–2.90 (m, 1H), 2.73 (m, 0.4H, rotamer); 2.46–2.64 (several peaks, 1.6H); 2.31 (m, 0.6H, rotamer); 2.15 (m, 0.4H, rotamer). $^{13}$C NMR (100 MHz; CD$_3$OD): δ 174.2; 173.4; 168.2.

Example 3

(R)-6-Chloro-4-hydroxy-1,1-dioxothiochromane-4-yl-C(O)-Aze-Pab (i) 6-Chloro-4-hydroxythiochromane-4-yl-carboxylic Acid, Methyl Ester The sub-title compound was prepared according to the method of C. F. Bigge et al. in J. Med. Chem., (1993), 36, 1977 from 6-chloro-4-thiochromanone (1.74 g, 8.76 mmol) using methanol instead of ethanol.

Yield: 0.625 g (28%). $^1$H NMR (500 MHz; CDCl$_3$) δ 7.07–7.15 (several peaks, 3H), 3.93 (s, 1H), 3.93 (s, 3H), 3.23 (ddd, 1H), 2.99 (ddd, 1H), 2.42 (ddd, 1H), 2.34 (ddd, 1H).

(ii) 6-Chloro-4-hydroxythiochromane-4-yl-carboxamide

The sub-title compound was obtained as the main product in the previous step and isolated using reversed phase HPLC (acetonitrile: 0.1 M aq. ammonium acetate).

Yield: 1.49 g (70%). $^1$H NMR (500 MHz; CDCl$_3$) δ 7.35 (d, 1H), 7.15 (dd, 1H), 7.09 (d, 1H), 6.32 (bs, 1H), 5.90 (bs, 1H), 3.86 (bs, 1H), 3.19 (ddd, 1H), 3.03 (ddd, 1H), 2.40 (ddd, 1H), 2.30 (ddd, 1H).

(iii) 6-Chloro-4-hydroxythiochromane-4-yl-carboxylic Acid

Potassium hydroxide (5.1 g, 91 mmol) and 6-chloro-4-hydroxythiochromane-4-yl-carboxamide (1.36 g, 5.58 mmol; from step (ii) above) were dissolved in water (25 mL) and isopropanol and refluxed for 2 d. The isopropanol was removed under reduced pressure and the aqueous residue was washed with diethyl ether. Acidification with aq. HCl, extraction with ethyl acetate, and then drying and concentration in vacuo afforded the sub-title compound. Yield: 0.87 g (64%).

MS(m/z) 243 (M−1)$^-$. Alternative method: The sub-title compound was also obtained using the method in Example 1(v) above, starting from 6-chloro-4-hydroxythiochromane-4-yl-carboxylic acid, methyl ester (0.63 g, 2.4 mmol; from step (i) above). Yield: 0.55 g (92%).

(iv) (R)-6-Chloro-4-hydroxythiochromane-4-yl-carboxylic Acid

The enantiomers of 6-chloro-4-hydroxythiochromane-4-yl-carboxylic acid (1.4 g, 5.7 mmol; from step (iii) above) were separated using chiral chromatography (Kromasil TBB; heptane: ethyl acetate: formic acid) yielding 0.500 g (71%) of the slower moving sub-title compound.

(v) (R)-6-Chloro-4-hydroxychromane-4-yl-C(O)-Aze-Pab (Teoc)

The sub-title compound was prepared analogously to the method described in Example 1(viii) (alternative preparation, first step) above, starting from (R)-6-chloro-4-hydroxychromane-4-yl-carboxylic acid (0.178 g, 0.727 mmol; from step (iv) above) and H-Aze-Pab(Teoc) (0.36 g, 0.80 mmol; prepared as described in international patent application WO 98/57932). Yield: 0.31 g (71%). MS(m/z) 601 (M−1)$^-$; 603 (M+1)$^+$.

(vi) (R)-6-Chloro-4-hydroxy-1,1-dioxothiochromane-4-yl-C(O)-Aze-Pab(Teoc)

The sub-title compound was prepared analogously to the method described in Example 1(viii) (alternative preparation, second step) above, starting from (R)-6-chloro-4-hydroxythio-chromane-4-yl-C(O)-Aze-Pab(Teoc) (0.113 g, 0.187 mmol; from step (v) above) and m-chloroperbenzoic acid (0.16 g of ~60%, 0.56 mmol). Yield: 0.029 g (27%). MS(m/z) 633 (M−1)$^-$, 635 (M+1)$^+$.

(vii) (R)-6-Chloro-4-hydroxy-1,1-dioxothiochromane-4-yl-C(O)-Aze-Pab×HOAc

The title compound was prepared analogously to the method described in Example 1(ix) above, starting from (R)-6-chloro-4-hydroxy-1,1-dioxothiochromane-4-yl-C(O)-Aze-Pab(Teoc) (0.029 g, 0.046 mmol; from step (vi) above) and tetrabutylammonium fluoride (0.080 mL of 1.0 M, 0.080 mmol).

Yield: 0.023 g (91%). MS(m/z) 489 (M−1)$^-$, 491 (M+1)$^+$. $^1$H NMR (400 MHz; CD$_3$OD): (complex due to diastereomers/rotamers) δ 7.47–7.84 (several peaks, 7H); 5.55 (dd, 0.3H, rotamer); 4.43–4.66 (several peaks, 2.7H); 4.30 (m, 0.7H, rotamer); 4.09 (m, 0.5H, rotamer); 4.00 (m, 0.5H, rotamer); 3.77 (ddd, 0.5H, rotamer); 3.54–3.67 (several peaks, 1.3H); 3.43 (ddd, 0.5H, rotamer); 2.52–2.99 (several peaks, 3H); 2.24–2.33 (m, 1H); 2.10–2.20 (m, 0.7H), rotamer), 1.92 (s, 3H), 1.75–1.85 (m, 0.3H), rotamer). $^{13}$C NMR (100 MHz; CD$_3$OD): (complex due to diastereomers/rotamers, carbonyl and/or amidine carbons) δ 173.5; 172.9; 168.1.

Example 4

(R)-6-Chloro-4-hydroxy-8-methoxy-1,1-dioxothiochromane-4-yl-C(O)-Aze-Pab(OBn)

(i) (R)-6-Chloro-4-hydroxy-8-methoxy-1,1-dioxothiochromane-4-yl-C(O)-Aze-Pab(OBn)(Teoc)

(R)-6-Chloro-4-hydroxy-8-methoxy-1,1-dioxothiochromane-4-yl-C(O)-Aze-Pab-(Teoc) (0.040 g, 0.060 mmol; see Example 1(viii) above) and O-benzylhydroxylamine×HCl (0.047 g, 0.29 mmol) in THF (15 mL) were heated to 60° C. for 2d. After concentration under reduced pressure, the residue was dissolved in ethyl acetate and washed with water and brine. Drying (MgSO$_4$) and removal of the solvent in vacuo afforded a colourless solid residue. Yield: 0.046 g (99%). MS(m/z) 771 (M+1)$^+$, 793 (M+23)$^+$.

(ii) (R)-6-Chloro-4-hydroxy-8-methoxy-1,1-dioxothiochromane-4-yl-C(O)-Aze-Pab(OBn)

A solution of (R)-6-chloro-4-hydroxy-8-methoxy-1,1-doxothjochromane-4-yl-C(O)-Aze-Pab(OBn)(Teoc) (0.046 g, 0.060 mmol; from step (i) above) and tetrabutylammonium fluoride (0.20 mL of 120 M, 0.20 mmol) in acetonitrile (3 mL) was heated to 60° C. for 3 h. After concentration under reduced pressure, the residue was dissolved in ethyl acetate and washed with water and brine. Evaporation of the solvent in vacuo afforded only 0.019 g. The aqueous fractions were freeze dried, combined with the evaporation residue from the organic phase and purified using reversed-phase HPLC (acetonitrile: 0.1 M aq. ammonium acetate) to afford, after freeze drying the appropriate fractions, the title compound as a colourless solid.

Yield: 0.00 9 g (24%). MS(m/z) 625 (M−1)$^-$, 627 (M+1)$^+$. $^1$H NMR (400 MHz; CDCl$_3$): δ 7.59 (d, 2H), 7.23–7.45 (several peaks, is 7H), 6.99 (d, 1H), 6.81 (d, 1H), 5.12 (s, 2H); 4.90 (dd, 1H), 4.85 (bs, 2H), 4.40–4.54 (AB-part of ABX-system, 2H), 4.09 (m, 1H), 3.97 (s, 3H), 3.84 (ddd, 1H), 3.28 (ddd, 1H), 3.09 (m, 1H), 2.79 (ddd, 1H), 2.63 (m, 1H), 2.32 (m, 1H), 2.21 (m, 1H). $^{13}$C NMR (100 MHz; CDCl$_3$): (carbonyl and/or amidine carbons) δ 169.1, 158.3, 151.6.

Example 5

(R)-6-Chloro-4-hydroxy-8-methoxy-1,1-dioxothiochromane-4-yl-C(O)-Aze-Pab(C(O)-O-cyclopentyl)

Sodium hydroxide (aq.; 0.5 B of 2.0 M, 1.0 9mol) was added to a solution of (R)-6-chloro-4-hydroxy-8-methoxy- 1,1-dioxothiochromane-4-yl-C(O)-Aze-PabxHOAC (21 mg, 40 μmol; see Example 1 above) and cyclopentyl chloroformate (11 mg, 74 μmol) in dichloromethane, and the mixture was stirred at rt for 3 h. After dilution with water, the resultant mixture was extracted with dichloromethane. The combined organic fractions were concentrated in vacuo and purified using flash chromatography (SiO$_2$; dichloromethane, then with EtOAc/MeOH 95/5). The fractions of interest were concentrated under reduced pressure, then dissolved in water/acetonitrile and freeze dried to afford the title compound. Yield: 16 mg (60%).

MS(m/z) 631 (M−1)$^-$, 633 (M+1)$^+$. $^1$H NMR (300 MHz; CDCl$_3$): (minor rotamer (~10%) not reported) δ 7.75 (d, 2H), 7.49 (t, 1H), 7.23 (d, 2H), 6.92 (d, 1H), 6.85 (d, 1H), 5.14 (m, 1H); 4.82 (broad dd, 2H), 4.34–4.58 (AB-part of ABX-system, 2H), 4.15 (m, 1H), 3.97 (bs, 1H), 3.92 (s, 3H), 3.71 (ddd, 1H), 3.39 (ddd, 1H), 3.24 (m, 1H), 2.79 (ddd, 1H), 2.56 (m, 1H), 2.22–2.38 (several peaks, 2H), 1.51–2.00 (several peaks, 8H). $^{13}$C NMR (100 MHz; CDCl$_3$): (carbonyl and/or amidine carbons) δ 173.1, 171.1, 169.3, 158.2.

Example 6

(R)-6,8-Dichloro-4-hydroxy-1,1-dioxothiochromane-4-yl-C(O)-Aze-Pab(OMe)

(i) (R)-6,8-Dichloro-4-hydroxy-1,1-dioxothiochromane-4-yl-C(O)-Aze-Pab(OMe)(Teoc)

(R)-6,8-Dichloro-4-hydroxy-1,1-dioxothiochromane-4-yl-C(O)-Aze-Pab(Teoc) (0.046 g, 0.069 mmol; from Example 2(viii) above) and O-methyl-hydroxylamine×HCl (0.043 g, 0.51 mmol) in THF (5 mL) were refluxed overnight. After concentration under reduced pressure, the residue was dissolved in ethyl acetate and washed with water and brine. Drying (MgSO$_4$) and removal of the solvent in vacuo afforded a colourless solid residue. Yield: 0.042 g (87%).

(ii) (R)-6,8-Dchloro-4-hydroxy-1,1-dioxothiochromane-4-yl-C(O)-Aze-Pab(OMe)

Trifluoroacetic acid (1.0 mL) was added to a stirred ice/water-cooled solution of (R)-6,8-dichloro-4-hydroxy-1,1-dioxothiochromane-4-yl-C(O)-Aze-Pab(OMe)(Teoc) (0.042 g, 0.060 mmol; from step (i) above) in dichloromethane (3 mL). The cooling bath was removed after 1 h. After 3 h at rt, acetonitrile was added and the solvents were carefully removed under reduced pressure. The crude product was purified using reversed-phase HPLC (acetonitrile:0.1 M aq. ammonium acetate) to afford, after freeze drying the appropriate fractions, the title compound as a colourless solid.

Yield: 0.018 g (54%). MS(m/z) 553 (M−1)$^-$, 555 (M+1)$^+$. $^1$H NMR (400 MHz; CDC)$_3$): (minor rotamer (~10%) not reported) δ 7.57 (d, 2H), 7.51 (d, 1H), 7.10–7.55 (several peaks, 4H), 4.96 (bs, 2H); 4.94 (dd, 1H), 4.38–4.54 (AB-part of ABX-system, 2H), 4.18 (m, 1H), 3.91 (s, 3H), 3.76 (ddd, 1H), 3.43 (ddd, 1H), 3.23 (m, 1H), 2.84 (ddd, 1H), 2.58 (m, 1H), 2.27–2.43 (several peaks, 2H). $^{13}$C NMR (100 MHz; CDCl$_3$): (carbonyl and/or amidine carbons) δ 172.7, 169.1, 151.5.

Example 7

6-Chloro-8-difluoromethoxy-4-hydroxy-1,1-dioxothiochromane-4-yl-C(O)-Aze-Pab (i) 6-Chloro-8-hydroxy-4-thiochromanone, Ethylene Ketal To a solution of 6-chloro-8-methoxy-4-thiochromanone (7.64 g, 33.4 mmol; see Example l(iii) above) in benzene (300 mL) under nitrogen was added ethylene glycol (9.34 mL, 167 mmol) and PTSA·H$_2$O (catalytic amount). The mixture was heated to reflux with a Dean-Stark trap for 48 h. In order to drive the reaction to completion it was necessary to add molecular sieves (type 4 Å, 8–12 mesh) to the trap. The reaction was cooled to room temperature, solid NaHCO$_3$ (0.10 g) was added and the mixture was diluted with EtOAc (200 mL). The organic layer was washed with saturated NaHCO$_3$ (2×150 mL), brine (150 mL), dried (Na$_2$SO$_4$), filtered, and concentrated in vacuo to afford 9.03 g (ca. 99%) of the intermediate ketal as a crude yellow solid. Ethanethiol (24.7 mL, 334 mmol) was added to a mixture of the above ketal (13.0 g, 47.7 mmol) in DMF (250 mL) under nitrogen and cooled to 0° C. Sodium hydride (8.0 g, 334 mmol) was added slowly and the reaction stirred at 0° C. for 15 minutes, then placed in an oil bath and heated to 135° C. for 1.5 h. Once the reaction had cooled to room temperature, it was poured into an ice-water mixture (300 g) containing saturated NH4Cl solution (70 mL). The aqueous layer was extracted with EtOAc (2×150 mL) and the combined organic extracts were washed with brine (200 mL), dried (Na$_2$SO$_4$), filtered, and concentrated in vacuo. The brown residue was chromatographed on silica gel eluting with CH$_2$Cl$_2$ to afford 11.3 g (92%) of the sub-title compound as a yellow solid.

$^1$H NMR (300 MHz, CD$_3$OD) δ 7.05 (s, 1H), 6.68 (s, 1H), 4.05–4.20 (m, 4H), 3.07 (t, J =8.0 Hz, 2H), 2.13 (t, J=8.0 Hz, 2H).

(ii) 6-Chloro-8-difluoromethoxy-4-thiochromanone, Ethylene Ketal

A solution of 6-chloro-8-hydroxy-4-thiochromanone, ethylene ketal (6.0 g, 23.2 mmol; from step (i) above) in 2-propanol (100 mL) and 30% KOH (50 mL) was heated to reflux and Freon 22 was bubbled directly into the reaction for 50 min. at <2.0 psi. The mixture was cooled to room temperature, partitioned between CH$_2$Cl$_2$ and H$_2$O (2:1, 450 mL) and the aqueous layer was extracted with CH$_2$Cl$_2$ (150 mL). The combined organic layers were washed with brine (150 mL), dried (Na$_2$SO$_4$), filtered, and concentrated in vacuo. The resulting residue was chromatographed on silica gel eluting with CH$_2$Cl$_2$ to afford 7.2 g (78%) of the sub-title compound as a yellow solid.

is $^1$H NMR (300 MHz, CDCl$_3$) δ 7.45 (s, 1H), 7.10 (s, 1H), 6.45 (t, J=74 Hz, 1H), 4.09–4.25 (m, 4H), 3.17 (t, J=7.5 Hz, 2H), 2.17 (t, J=7.5 Hz, 2H).

(iii) 6-Chloro-8-difluoromethoxy-4-thiochromanone

A solution of 6-chloro-8-difluoromethoxy-4-thiochromanone, ethylene ketal (5.11 g, 16.6 mmol; from step (ii) above) in THF (105 mL) and 0.5 N HCl (70 mL) was stirred at room temperature for 96 h. The reaction was neutralized with saturate d NaHCO$_3$ (150 mL) and extracted with CH$_2$Cl$_2$ (2×100 mL). The combined organic extracts were washed with brine (100 mL), dried (Na$_2$SO$_4$), filtered, and concentrated in vacuo to afford 4.40 g (ca. 100%) of the sub-title compound as a yellow solid which was used without further purification.

$^1$H NMR (300 MHz, CDCl$_3$) δ 8.00 (s, 1H), 7.30 (s, 1H), 6.56 (t, J=74 Hz, 1H), 3.24 (t, J=7.5 Hz, 2H), 3.00 (t, J=7.5 Hz, 2H).

(iv) 6-Chloro-8-difluoromethoxy-4-methylenethiochromane

A solution of 6-chloro-8-difluoromethoxy-4-thiochromanone (2.5 g, 9.40 mmol; from step (iii) above) in anhydrous Et$_2$O (150 mL) was cooled to 0° C. under nitrogen. Tebbe Reagent (21.0 mL of 0.5M in toluene, 10.3 mmol) was added dropwise via syringe, and the mixture was stirred at 0° C. for 2 h and then stirred at room temperature for 1 h. The reaction was cooled to 0° C. and slowly quenched with MeOH (ca. 50 mL) until the solution solidified. The mixture was diluted with EtOAc/H₂O (4:1, 100 mL) and filtered through a pad of Celite. The Celite was washed with EtOAc (800 mL) and the filtrate was concentrated in vacuo. The crude dark red oil was chromatographed on silica gel eluting with Hex:EtOAc (4:1) to afford 0.88 g (36%) of sub-title compound as a dark yellow oil. $^1$H NMR (300 MHz, CDCl₃) δ 7.40 (s, 1H), 7.05 (s, 1H), 6.46 (t, J=75 Hz, 1H), 5.53 (s, 1H), 5.10 (s, 1H), 3.06 (t, J=7.5 Hz, 2H), 2.80 (t, J=7.5 Hz, 2H).

(v) (R)-6-Chloro-8-difluoromethoxy-4-hydroxy-4-hydroxymethylthiochromane

2-Methyl-2-propanol (120 mL), H₂O (120 mL), and AD-mix-β (13.3 g) were combined together and cooled to 0° C. Concurrently, 6-chloro-8-difluoromethoxy-4-methylenethiochromane (2.65 g, 10.1 mmol; from step (iv) above) was cooled to −5° C. in an ice/MeOH bath. Once sufficiently cooled, the AD-mix-β solution was added and stirred at <0° C. for 2 h, then at room temperature for 4 h. The reaction was quenched with solid sodium sulfite (ca. 5.0 g) resulting in a clear solution which was then partitioned between EtOAc/H₂O (1:1, 300 mL) and further extracted with EtOAc (100 mL). The organic extracts were combined and washed with 5 M H₂SO₄ (75 mL), saturated NaHCO₃ (150 mL), and brine (150 mL), dried (Na₂SO₄), filtered, and concentrated in vacuo to afford 2.99 g (ca. 100%) of the sub-title compound as a yellow solid which was used without further purification. $^1$H NMR (300 MHz, CD₃OD) δ 7.55 (s, 1H), 7.08 (s, 1H), 6.78 (t, J=75 Hz, 1H), 3.70 (d, J=12 Hz, 1H), 3.50 (d, J=12 Hz, 1H), 2.97–3.20 (m, 2H), 2.46–2.55 (m, 1H), 1.91–2.02 (m, 1H).

(vi) (R)-6-Chloro-8-difluoromethoxy-4-hydroxythiochromane-4-yl-carboxylic Acid

Sodium carbonate (0.72 g, 6.7 mmol) and 5% Pt/C (1.50 g, 75% weight of reactant) were added to a solution of (R)-6-chloro-8-difluoromethoxy-4-hydroxy-4-hydroxymethylthiochromane (2.0 g, 6.7 mmol; from step (v) above) in H₂O (180 mL). The mixture was vigorously stirred at ca. 95° C. for 20–40 h with air being directly bubbled into the reaction mixture. The reaction was cooled to room temperature and filtered through a pad of Celite with saturated Na₂CO₃ solution (ca. 100 mL). The resulting liquid was slowly acidified with 2 N HCl (ca. 200 mL) and extracted with EtOAc (2×100 mL). The combined organic layers were washed with brine (75 mL), dried (Na₂SO₄), filtered, and concentrated in vacuo to afford 1.56 g (ca. 75%) of the sub-title compound as a brown oil which was used without further purification.

$^1$H NMR (300 MHz, CD₃OD) δ 7.24 (s, 1H), 7.12 (s, 1H), 6.81 (t, J=75 Hz, 1H), 3.04–3.19 (m, 2H), 2.40–2.50 (m, 1H), 2.25–2.35 (m, 1H).

(vii) (R)-6-Chloro-8-difluoromethoxy-4-hydroxy-1,1-dioxothiochromane-4-yl-carboxylic Acid A mixture of (R)-6-chloro-8-difluoromethoxy-4-hydroxythiochromane-4-yl-carboxylic acid (0.50 g, 1.6 mmol; from step (vi) above), wet alumina (prepared by adding H₂O (1 mL) to alumina (5.0 g) and shaking until a free flowing powder was obtained, ca. 0.82 g, 8.0 mmol), and Oxone® (4.9 g, 8.0 mmol) in CHCl₃ (19 mL) was heated to 40–45° C. for 20 h. The reaction was cooled to room temperature, filtered through a Buichner funnel with EtOAc (50 mL), and concentrated in vacuo to afford 0.54 g (98%) of the sub-title compound as a brown foam which was used without further purification.

$^1$H NMR (300 MHz, CD₃OD) δ 7.44 (s, 2H), 6.94 (t, J=75 Hz, 1H), 3.61–3.75 (m, 2H), 2.81–2.91 (m, 1H), 2.52–2.62 (m, 1H).

(viii) (R)-6-Chloro-8-difluoromethoxy-4-hydroxy-1,1-dioxothiochromane-4-yl-C(O)-Aze-Pab(Teoc)

To a solution of (R)-6-chloro-8-difluoromethoxy-4-hydroxy-1,1-dioxothiochromane-4-yl-carboxylic acid (0.54 g, 1.6 mmol; from step (vii) above) in DMF (20 mL) under argon at 0° C. was added H-Aze-Pab(Teoc)×HCl (0.92 g, 2.1 mmol), PyBOP (0.91 g, 1.7 mmol), and Hünig's Base (0.7 mL, 4.0 mmol). The reaction was stirred at 0° C. for 2 h and then at room temperature for 20 h. The mixture was concentrated under reduced pressure and the residue was chromatographed twice on silica gel, eluting first with CHCl₃:EtOH (10:1) and then with EtOAc:EtOH (10:1) to afford 0.44 g (40%) of the sub-title compound as a yellow crystalline solid.

mp 135–145° C. $^1$H NMR (300 MHz, CD₃OD, complex mixture of rotamers) δ 7.74–7.82 (m, 2H), 7.36–7.59 (m, 4H), 6.81 (t, J=75 Hz, 1H), 5.48–5.55 and 4.80–4.89 (m, 1H), 4.71–3.39 (m, 8H), 2.90–2.10 (m, 4H), 1.08 (m, 2H), 0.10 (s, 9H). APCI-MS(m/z) 701 (M+1)⁺.

(ix) (R)-6-Chloro-8-difluoromethoxy-4-hydroxy-1,1-dioxothiochromane-4-yl-C(O)-Aze-PabxHOAc Trifluoroacetic acid (3.0 mL) was added to a stirred ice/water-cooled solution of (R)-6-chloro-8-difluoromethoxy-4-hydroxy-1,1-dioxothiochromane-4-yl-Aze-Pab(Teoc) (71 mg; 0.10 mmol; from step (viii) above) in methylene chloride (1 mL). After 1 h methylene chloride (3 mL) was added and the solvents were carefully removed under reduced pressure. The residue was dissolved in water/acetonitrile and freeze dried. Purification with reversed-phase HPLC (0.1M aq. ammonium acetate/acetonitrile, 7:3) afforded the title compound as a white solid.

Yield: 45 mg (72%). APCI-MS(m/z) 557 (M+1)⁺, 555 (M−1)⁻. $^1$H NMR (400 MHz; CD₃OD): δ 7.77 (complex due to diastereomers/rotamers) (d, 0.8H, rotamer); 7.68 (d, 1.2H, rotamer); 7.58 (d, 0.6H, rotamer); 7.55 (d, 0.8H, rotamer); 7.48 (d, 1.2H, rotamer); 7.47 (d, 0.4H, rotamer); 7.40 (m, 0.4H, rotamer); 7.38 (m, 0.6H, rotamer); 6.90 (t, 1H); 5.54 (dd, 0.4H, rotamer); 4.68 (m, 0.6H, rotamer); 4.35–4.61 (several peaks, 3H); 4.09 (m, 0.4H, rotamer); 3.99 (m, 0.6H, rotamer); 3.82 (apparent dt, 0.4H, rotamer); 3.65 (apparent t, 1.2H, rotamer); 3.44 (m, 0.4H, rotamer); 2.69–2.90 (several peaks, 1.4H); 2.48–2.64 (several peaks, 1.6H); 2.29 (m, 0.6H, rotamer); 2.15 (m, 0.4H, rotamer); 1.89 (s, 3H).

$^3$C NMR (75 MHz; CD₃OD): (complex due to diastereomers/rotamers, carbonyl and/or amidine carbons) ↓ 174.1; 173.4; 173.3; 172.9; 168.1.

Example 8

6-Chloro-4-(R)-hydroxy-8-methoxy-1-(R or S)-oxo-thiochromane-4-yl-C(O)-Aze-PabxTFA (i) 6-Chloro-4-(R)-hydroxy-8-methoxy-1-(R or S)-oxo-thiochromane-4-yl-carboxylic acid (I) and 6-Chloro-4-(R)-hydroxy-8-methoxy-1-(S or R)-oxo-thiochromane-4-yl-carboxylic Acid (II)

A mixture of (R)-6-chloro-4-hydroxy-8-methoxythiochromane-4-yl-carboxylic acid (700 mg, 2.60 mmol, see Example 1(vi) above) and 35% H₂O₂ (3.4 mL, 30.1 mmol) in CH₂Cl₂ (40 mL) was stirred at 0° C. for 2 h, and then overnight at 25° C. under nitrogen. The mixture was concentrated in vacuo and chromatographed on silica gel eluting with CHCl₃:MeOH:concentrated NH₄OH (7.5:2.0:0.5) to afford 320 mg of the ammonium salt of the sub-title compound diastereomer (I) and 190 mg of the ammonium salt of the sub-title compound diastereomer (II). Both materials were each separately dissolved in H₂O (40 mL), acidified with 1N HCl, and extracted with EtOAc (2×50 mL). The organic extracts of each were dried (Na₂SO₄), filtered, and concentrated to afford 290 mg (40%)

of sub-title compound (I) and 170 mg (22%) of sub-title compound (II), respectively.

For sub-title compound diastereomer (I): ¹H NMR (300 MHz, CD₃OD) δ 7.25 (s, 1H), 7.05 (s, 1H), 4.00 (s, 3H), 3.60–3.68 (m, 1H), 3.20–3.28 (m, 1H), 2.80–2.92 (m, 1H), 2.46–2.58 (m, 1H) APCI-MS: (M+1)=291 m/z For sub-title compound diastereomer (II):
¹H NMR (300 MHz, CD₃OD) δ 7.35 (s, 1H), 7.20 (s, 1H), 4.00 (s, 3H), 3.42–3.58 (m, 1H), 3.18–3.30 (m, 1H), 2.70–2.88 (m, 1H), 2.30–2.45 (m, 1H). APCI-MS: (M+1)= 291 m/z (ii) 6-Chloro-4-(R)-hydroxy-8-methoxy-1-(R or S)-oxo-thiochromane-4-yl-C(O)-Aze-Pab(Teoc)

To a solution of 6-chloro-4-(R)-hydroxy-8-methoxy-1-(R or S)-oxo-thiochromane-4-yl-carboxylic acid (diastereomer (I) from step (i) above, 284 mg, 0.98 mmol) in DMF (10 mL) under nitrogen was added H-Aze-Pab(Teoc)×HCl (571 mg, 1.27 mmol), PyBOP (559 mg, 1.07 mmol), and DIPEA (315 mg, 2.44 mmol) at 0° C. The reaction was stirred at 0° C. for 2 h and then at room temperature overnight. The mixture was concentrated in vacuo and the residue chromatographed twice on silica gel, eluting twice with CHCl₃:EtOH (9:1) to afford 190 mg (30%) of the sub-title compound as a white solid.

mp: 225–230° C. $R_f$=0.57 (9:1 CHCl₃:EtOH) ¹H NMR (300 MHz, CD₃OD/CDCl₃ (1:1), complex mixture of rotamers) δ 7.83 (d, J=8 Hz, 2H), 7.38 (d, J=7 Hz, 2H), 7.08 (s, 1H), 6.99 (s, 1H), 4.87–4.92 (m, 1H), 4.51–4.54 (m, 2H), 4.21–4.30 (m, 4H), 4.00 (s, 3H), 3.12–3.39 (m, 4H), 2.39–2.50 (m, 1H), 2.16–2.22 (m, 1H), 1.08–1.14 (m, 2H), 0.08 (s, 9H) APCI-MS: (M+1)=649 m/z.

(iii) 6-Chloro-4-(R)-hydroxy-8-methoxy-1-(R or S)-oxo-thiochromane-4-yl-C(O)-Aze-PabxTFA To a solution of 6-chloro-4-(R)-hydroxy-8-methoxy-1-(R or S)-oxo-thiochromane-4-yl-C(O)-Aze-Pab(Teoc) (90 mg, 0.14 mmol, from step (ii) above) in dichloromethane (2 mL), trifluoroacetic acid (2 mL) was added. The solution was left at ambient temperature for 1 h whereupon it was concentrated under reduced pressure. The residue was dissolved in deionized water and freeze dried. Yield: 80 mg (0.13 mmol).

¹H-NMR (500 MHz; CD₃OD): (complex mixture due to rotamers) δ 8.75 (t, 0.75H, rotamer); 8.63 (t, 0.25H, rotamer); 7.76 (d, 0.5H, rotamer); 7.72 (d, 1.5H, rotamer); 7.55 (d, 2H, mix of rotamers); 7.23 (s, 1H, mix of rotamers); 7.11 (s, 0.75H, rotamer); 7.01 (s, 0.25H, rotamers); 5.45 (m, 0.5H); 4.61 (m, 1H); 4.47 (m, 2H); 4.13 (dm, 0.5H); 3.98 (s, 3H); 3.83 (q, 1H); 3.23 (m, 1.5H); 3.10 (m, 1.25H); 2.97 (m, 0.25H); 2.78 (m, 0.25H); 2.49 (m, 0.75H); 2.26 (m, 1H); 2.18 (m, 1H) MS (m/z) 505 (M+1)⁺, 503 (M-1)⁻.

Example 9

6-Chloro-4-(R)-hydroxy-8-methoxy-1-(S or R)-oxo-thiochromane-4-yl-C(O)-Aze-PabxTFA (i) 6-Chloro-4-(R)-hydroxy-8-methoxy-1-(S or R)-oxo-thiochromane-4-yl-C(O)-Aze-Pab(Teoc)

To a solution of 6-chloro-4-(R)-hydroxy-8-methoxy-1-(S or R)-oxo-thiochromane-4-yl-carboxylic acid (diastereomer (II) from Example 8(i) above, 166 mg, 0.57 mmol) in DMF (10 mL) under nitrogen were added H-Aze-Pab(Teoc)×HCl (333 mg, 0.74 mmol), PyBOP (327 mg, 0.63 mmol), and DIPEA (184 mg, 1.43 mmol) at 0° C. The reaction was stirred at 0° C. for 2 h and then at room temperature overnight. The mixture was concentrated in vacuo and the residue chromatographed twice on silica gel, eluting first with CHCl₃:EtOH (9:1) and second with CHCl₃:MeOH (20:1) to afford 80 mg (22%) of the sub-title compound as a white solid.

mp: 140–145° C. $R_f$=0.60 (9:1 CHCl₃:EtOH) ¹H NMR (300 MHz, CD₃OD, complex mixture of rotamers) δ 7.80 and 7.72 (d, J=8 Hz, 2H), 7.42–7.49 (m, 2H), 7.32 (s, 1H), 7.17 (s, 1H), 5.52–5.57 (m, 1H), 4.44–4.91 (m, 4H), 4.19–4.25 (m, 2H), 3.97 (s, 3H), 3.00–3.72 (m, 3H), 2.10–2.82 (m, 3H), 1.04–1.11 (m, 2H), 0.07 (s, 9H) APCI-MS: (M+1)=649 m/z.

(ii) 6-Chloro-(R)-4-(R)-hydroxy-8-methoxy-1-(S or R)-oxo-thiochromane-4-yl-C(O)-Aze-PabxTFA To a solution of 6-chloro-4-(R)-hydroxy-8-methoxy-1-(S or R)-oxo-thiochromane-4-yl-C(O)-Aze-Pab(Teoc) (35 mg, 0.054 mmol from step (i) above) in dichloromethane (2 mL), was added trifluoroacetic acid (2 mL). The solution was left at ambient temperature for 1 h whereupon it was concentrated at reduced pressure. The residue was dissolved in deionized water and freeze dried. Yield: 30 mg (0.048 mmol).

¹H-NMR (500 MHz; CD₃OD): (complex mixture due to rotamers) δ 548.82 (m, 0.2H); 8.65 (m, 0.2H); 7.77 (d, 0.9H); 7.66 (d, 0.8H); 7.59 (d, 0.9H); 7.43 (d, 0.8H); 7.40 (d, 0.4H); 7.30 (d, 0.4H); 7.16 (dd, 0.8H); 5.55 (m, 0.45H); 4.70 (m, 0.6H); 4.59 (m, 0.6H); 4.51 (m, 1.8H); 4.05 (q, 0.45H); 3.97 (s, 3H); 3.94 (m, 0.4H); 3.58 (m, 0.4H); 3.38 (m, 0.4H); 3.16 (m, 0.4H); 3.03 (m, 0.4H); 2.75 (m, 0.8H); 2.58 (m, 0.4H); 2.45 (m, 1.2H); 2.30 (m, 0.4H); 2.15 (m, 0.45H) MS (m/z): 505 (M+1)⁺, 503 (M-1)⁻.

Example 10

Title compounds of Examples 1, 2, 3, 7, 8 and 9 were tested in Test A above and were found to exhibit an IC₅₀TT value of less than 0.05 μM.

Example 11

Title compounds of Examples 4, 5 and 6 are tested in Test E above and are found to exhibit oral and/or parenteral bioavailability in the rat as the corresponding active inhibitor (free amidine).

Example 12

Title compounds of Examples 4, 5 and 6 are tested in Test G above and are found to exhibit oral and/or parenteral bioavailability in the rat as the corresponding active inhibitor (free amidine).

| Abbreviations | |
|---|---|
| Ac | = acetyl |
| AcOH | = acetic acid |
| API | = atmospheric pressure ionisation (in relation to MS) |
| aq. | = aqueous |
| AUC | = area under the curve |
| Aze | = (S)-azetidine-2-carboxylate (unless otherwise specified) |
| AzeOH | = azetidine-2-carboxylic acid |
| Bn | = benzyl |
| BSA | = bovine serum albumin |
| CI | = chemical ionisation (in relation to MS) |
| d | = day(s) |
| DCC | = dicyclohexyl carbodiimide |
| DIPEA | = diisopropylethylamine |
| DMAP | = 4-(N,N-dimethyl amino) pyridine |
| DMF | = dimethylformamide |
| DMSO | = dimethylsulfoxide |
| EDC | = 1-(3-dimethylaminopropyl)-3-ethylcarbodiimide hydrochloride |
| Et | = ethyl |
| ether | = diethyl ether |

Abbreviations

| | | |
|---|---|---|
| EtOAc | = | ethyl acetate |
| EtOH | = | ethanol |
| h | = | hour(s) |
| HATU | = | O-(azabenzotriazol-1-yl)-N,N,N',N'-tetramethyluronium hexafluorophosphate |
| HBTU | = | [N,N,N',N'-tetramethyl-O-(benzotriazol-1-yl)uronium hexafluorophosphate] |
| HCl | = | hydrochloric acid, hydrogen chloride gas or hydrochloride salt (depending on context) |
| Hex | = | hexanes |
| HOAc | = | acetic acid |
| HPLC | = | high performance liquid chromatography |
| LC | = | liquid chromatography |
| Me | = | methyl |
| MeOH | = | methanol |
| min. | = | minutes |
| MS | = | mass spectroscopy |
| MTBE | = | methyl tert-butyl ether |
| NADH | = | nicotinamide adenine dinucleotide, reduced form |
| NADPH | = | nicotinamide adenine dinucleotide phosphate, reduced form |
| NIH | = | National Institute of Health (US) |
| NIHU | = | National Institute of Health units |
| Pab | = | para-amidinobenzylamino |
| H-Pab | = | para-amidinobenzylamine |
| PTSA | = | para-toluenesulphonic acid |
| PyBOP | = | (benzotriazol-1-yloxy)tripyrrolidinophosphonium hexafluorophosphate |
| RPLC | = | reverse phase high performance liquid chromatography |
| rt | = | room temperature |
| SOPs | = | standard operating procedures |
| TBTU | = | [N,N,N',N'-tetramethyl-O-(benzotriazol-1-yl)uronium tetrafluoroborate] |
| TEA | = | triethylamine |
| Teoc | = | 2-(trimethylsilyl)ethoxycarbonyl |
| TFA | = | trifluoroacetic acid |
| THF | = | tetrahydrofuran |
| THP | = | tetrahydropyranyl |
| TLC | = | thin layer chromatography |
| TMSCN | = | trimethylsilyl cyanide |
| Z | = | benzyloxycarbonyl |

Prefixes n, s, i and t have their usual meanings: normal, secondary, iso and tertiary.

What is claimed is:

1. A compound of formula I,

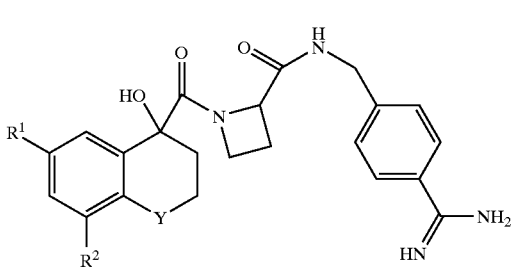

wherein
Y represents S(O) or S(O)$_2$;
$R^1$ represents halo; and
$R^2$ represents H, halo or $C_{1-4}$ alkoxy which latter group is optionally substituted by one or more halo groups;
or a pharmaceutically acceptable salt or prodrug thereof.

2. A compound as claimed in claim 1, wherein $R^1$ represents chloro.

3. A compound as claimed in claim 1, wherein $R^2$ represents H, halo or $C_{1-2}$ alkoxy which latter group is optionally substituted by one or more halo groups.

4. A compound as claimed in claim 1, wherein $R^1$ represents chloro and $R^2$ represents H, chloro, $OCH_3$, $OCHF_2$ or $OCF_3$.

5. A compound as claimed in claim 4, wherein $R^2$ represents $OCH_3$.

6. (R)-6-Chloro-4-hydroxy-8-methoxy-1,1-dioxothiochromane-4-yl-C(O)-(S)-Aze-Pab or a pharmaceutically acceptable salt or prodrug thereof.

7. A process for the preparation of a compound as claimed in claim 1, which comprises:

(i) the coupling of a compound of formula III,

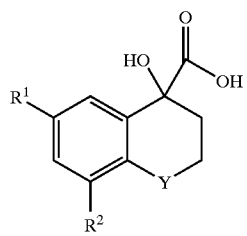

wherein Y, $R^1$ and $R^2$ are as defined in claim 1, with 4-amidinobenzyl-2-azetidinecarboxamide;

(ii) the coupling of a compound of formula IV,

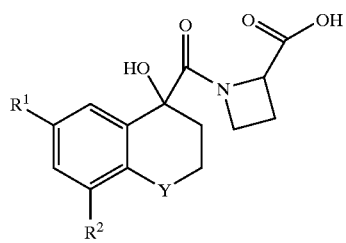

wherein Y, $R^1$ and $R^2$ are as defined in claim 1, with para-amidino-benzylamine; (iii) complete or partial oxidation of a corresponding compound of formula V,

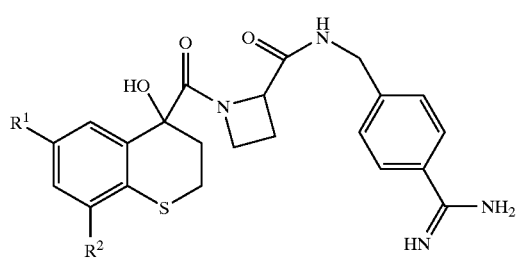

wherein $R^1$ and $R^2$ are as defined in claim 1;

(iv) deprotection of a protected compound of formula I as defined in claim 1; or (v) introduction or interconversion of a substituent on the aromatic ring in a compound of formula I as defined in claim 1.

8. A pharmaceutically acceptable compound of formula IA,

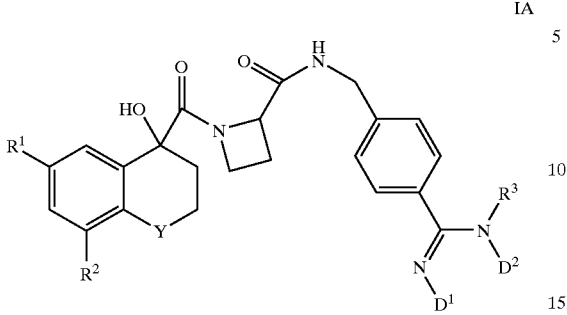

wherein
Y, $R^1$ and $R^2$ are as defined in claim 1;
$D^1$ and $D^2$ independently represent H, —$OR^7$ or $R^8$, or $D^1$, $D^2$ and $R^3$ together with the amidine group to which they are attached, form a cyclic group of formula IIa, IIb, IIc, IId or IIe,

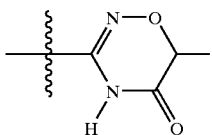

IIa

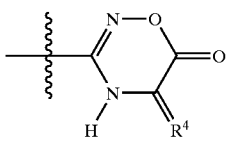

IIb

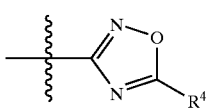

IIc

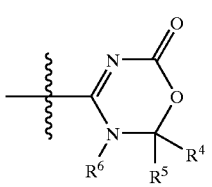

IId

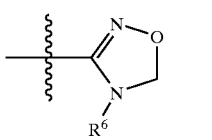

IIe wherein wavy lines indicate the points of attachment to the benzene ring;
$R^3$ represents H, or $R^3$, $D^1$, and $D^2$ together with the amidine group to which they are attached, form a cyclic group of formula Ia, IIb, IIc, IId or IIe;
$R^4$ and $R^5$ independently represent H or $C_{1-4}$ alkyl;
$R^6$ represents H, $C_{1-6}$ alkyl which latter group is optionally substituted by one or more halo groups or C(O)$OR^{12}$;
$R^7$ represents H, $C_{6-10}$ aryl, $C_{1-10}$ alkyl which latter group is optionally substituted by one or more halo groups, $C_{1-3}$ alkylphenyl, —C($R^{9a}$)($R^{9b}$)$R^{10}$, —C(O)$R^{11a}$, —C(O)$OR^{12}$, —C(O)N($R^{13}$)$R^{14}$ or —(CH$_2$)$_n$(O)$_m$$R^{15}$;

$R^8$ represents —C($R^{9a}$)($R^{9b}$)$R^{10}$, —C(O)$R^{11b}$ or —C(O)$OR^{12}$;
$R^{9a}$ and $R^{9b}$ independently represent, at each occurrence, H or $C_{1-6}$ alkyl;
$R^{10}$ represents, at each occurrence, —OC(O)$R^{16a}$, —OC(O)$OR^{17}$, —N($R^{18a}$)C(O)$OR^{17}$ or —OC(O)N($R^{18b}$)$R^{17}$;
$R^{11a}$ and $R^{11b}$ independently represent, at each occurrence, $C_{6-10}$ aryl, $C_{1-3}$ alkylphenyl which latter two groups are optionally substituted by one or more substituents selected from $C_{1-6}$ alkyl and halo, —[C($R^{19a}$)($R^{19b}$)]$_p$OC(O)$R^{16b}$, or $R^{11a}$ represents $C_{1-17}$ alkyl optionally substituted by $C_{1-6}$ alkoxy, $C_{1-6}$ acyloxy, amino or halo or $R^{11b}$ represents $C_{1-6}$ alkyl;
$R^{12}$ represents, at each occurrence, $C_{1-17}$ alkyl optionally substituted by one or more substituents selected from $C_{1-6}$ alkoxy, $C_{1-6}$ acyloxy, —Si($R^{20a}$)($R^{20b}$)($R^{20c}$) and halo, $C_{6-10}$ aryl, $C_{1-3}$ alkylphenyl which latter two groups are optionally substituted by $C_{1-6}$ alkyl, $C_{1-6}$ alkoxy, cyano or halo, —[C($R^{19a}$)($R^{19b}$)]$_q$OC(O)$R^{16b}$ or —CH$_2$$R^{21}$;
$R^{13}$ represents H or $C_{1-7}$ alkyl, or together with $R^{14}$ represents $C_{4-5}$ alkylene;
$R^{14}$ represents $C_{6-10}$ aryl or $C_{1-10}$ alkyl which latter group is optionally substituted by one or more substituents selected from OH, halo, $CO_2H$, $C_{1-6}$ alkoxy, $C_{1-6}$ acyloxy and $C_{6-10}$ aryl, or together with $R^{13}$ represents $C_{4-5}$ alkylene;
$R^{15}$ represents $C_{1-7}$ alkyl optionally substituted by one or more —OC(O)C(H)($R^{22}$)N(G)($G^a$) groups;
$R^{16a}$, $R^{16b}$ and $R^{17}$ independently represent, at each occurrence, $C_{6-10}$ aryl or $C_{1-17}$ alkyl which latter group is optionally substituted by one or more substituents selected from —OH, halo, —$CO_2H$, $C_{1-6}$ alkoxy, $C_{1-6}$ acyloxy and $C_{6-10}$ aryl, or $R^{16b}$ represents $C_{1-6}$ alkoxy optionally substituted by one or more substituents selected from $C_{1-6}$ alkyl and halo;
$R^{18a}$ and $R^{18b}$ independently represent H or $C_{1-4}$ alkyl;
$R^{19a}$ and $R^{19b}$ independently represent, at each occurrence, H or $C_{1-6}$ alkyl;
$R^{20a}$ to $R^{20c}$ independently represent, at each occurrence, $C_{1-6}$ alkyl or phenyl;
$R^{21}$ represents the structural fragment IIf

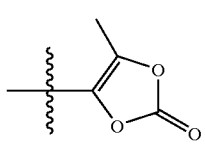

IIf $R^{22}$ represents $C_{3-4}$ alkyl;
G and $G^a$ independently represent H, an amino protective group, or G and
$G^a$ together represent an amino protective group;
m represents 0 or 1;
n represents 1, 2 or 3;
p represents 3 or 4;
q represents 2 or 3;
or a pharmaceutically acceptable salt thereof, provided that:
(a) $D^1$ and $D^2$ do not both represent H; and
(b) when one of $D^1$ and $D^2$ represents —$OR^7$, then the other represents H.

9. A compound as defined in claim 1, wherein the fragment

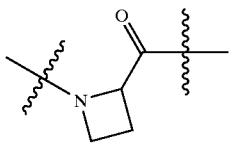

is in the S-configuration.

10. A compound as claimed in claim 1, wherein the fragment

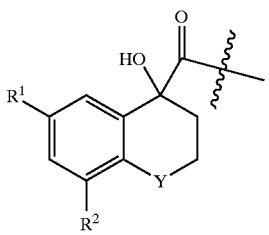

is in the R-configuration.

11. A process for the preparation of a compound as claimed in claim 8, which comprises:

(1) for compounds of formula IA in which one of $D^1$ and $D^2$ represents —$OR^7$ in which $R^7$ represents H, $C_{6-10}$ aryl, $C_{1-10}$ alkyl which latter group is optionally substituted by one or more halo groups, or $C_{1-3}$ alkylphenyl, reaction of a compound of formula XIV,

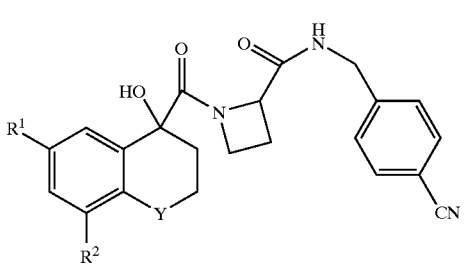

XIV wherein Y, $R^1$ and $R^2$ are as defined in claim 8, with a compound of formula XV,

 XV wherein $R^a$ represents H, $C_{6-10}$ aryl, $C_{1-10}$ alkyl which latter group is optionally substituted by one or more halo groups, or $C_{1-3}$ alkylphenyl, optionally by pre-treating the compound of formula XIV with gaseous HCl, in the presence of a lower alkyl alcohol to form a compound of formula XVI,

XVI

wherein $R^b$ represents lower alkyl and Y, $R^1$ and $R^2$ are as defined in claim 8;

(2) for compounds of formula IA in which one of $D^1$ and $D^2$ represents —$OR^7$ in which $R^7$ represents H, $C_{6-10}$ aryl, $C_{1-10}$ alkyl which latter group is optionally substituted by one or more halo groups, or $C_{1-3}$ alkylphenyl, reaction of a corresponding compound of formula IA, in which one of $D^1$ and $D^2$ represents —$C(O)OR^{12}$ and the other represents H, with a compound of formula XV, as defined above, followed by removal of the —$C(O)OR^{12}$ group;

(3) for compounds of formula IA in which $D^1$ or $D^2$ represents $R^8$, reaction of a corresponding compound of formula I, or a corresponding compound of formula IA in which $D^1$ or $D^2$ as appropriate represents H, with a compound of formula XVII, $L^3$—$R^8$           XVII wherein $L^3$ represents a leaving group and $R^8$ is as defined in claim 8;

(4) for compounds of formula IA in which one of $D^1$ and $D^2$ represents —$OR^7$ wherein $R^7$ does not represent H, reaction of a corresponding compound of formula IA in which one of $D^1$ and $D^2$ represents —OH with a compound of formula XVIII, $L^3$—$R^{7a}$           XVIII wherein $R^{7a}$ represents $R^7$ as defined in claim 8, except that it does not represent H, and $L^3$ is as defined above; (5) for compounds of formula IA in which one of $D^1$ and $D^2$ represents H and the other represents —$C(R^{9a})(R^{9b})R^{10}$, wherein $R^{10}$ represents —$OC(O)R^{16a}$, —$OC(O)OR^{17}$ or —$OC(O)N(R^{18b})R^{17}$, reaction of a corresponding compound of formula XIX,

XIX

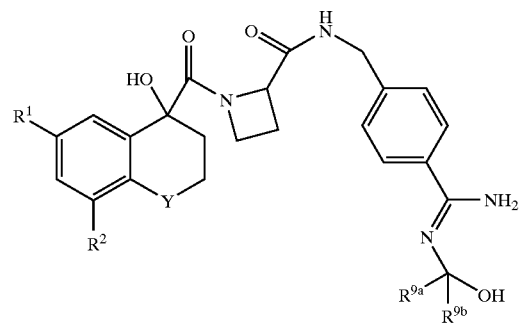

wherein Y, $R^1$, $R^2$, $R^{9a}$ and $R^{9b}$ are as defined in claim 8, with a compound of formula XX, $$L^3—C(O)R^c \qquad XX$$

wherein $R^c$ represents $R^{16a}$, —$OR^{17}$ or —$N(R^{8b})R^{17}$, and $R^{16a}$, $R^{17}$ and $R^{18b}$ are as defined in claim 8 and $L^3$ is as defined above;

(6) for compounds of formula IA in which $D^1$, $D^2$ and $R^3$, together with the amidine group to which they are attached, represent a group IIa as defined in claim 8, reaction of a corresponding compound of formula IA in which $D^1$ represents OH with a compound of formula XXII, $$HalC(O)CH(R^4)Hal \qquad XXII$$

wherein Hal represents halo and $R^4$ is as defined in claim 8, followed by cyclisation of the resultant intermediate;

(7) for compounds of formula IA in which $D^1$, $D^2$ and $R^3$, together with the amidine group to which they are attached, represent a group IIb as defined in claim 8, reaction of a corresponding compound of formula XXIII,

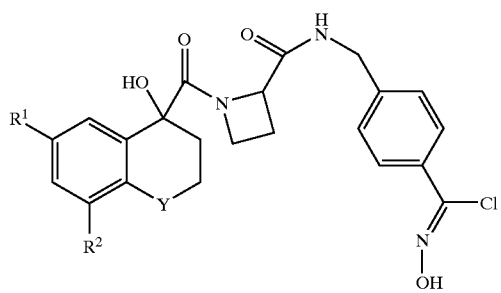

XXIII wherein Y, $R^1$ and $R^2$ are as defined in claim 8, with a compound of formula XXIV, $$H_2NCH(R^4)C(O)OR^b \qquad XXIV$$

wherein $R^b$ is as defined above and $R^4$ is as defined in claim 8;

(8) for compounds of formula IA in which $D^1$, $D^2$ and $R^3$, together with the amidine group to which they are attached, represent a group IIc as defined in claim 8, reaction of a corresponding compound of formula IA in which $D^1$ represents OH with a compound of formula XXV, $$R^4CHO \qquad XXV$$

wherein $R^4$ is as defined in claim 8;

(9) for compounds of formula IA in which $D^1$, $D^2$ and $R^3$, together with the amidine group to which they are attached, represent a group IId as defined in claim 8, cyclisation of a compound of formula XXVI,

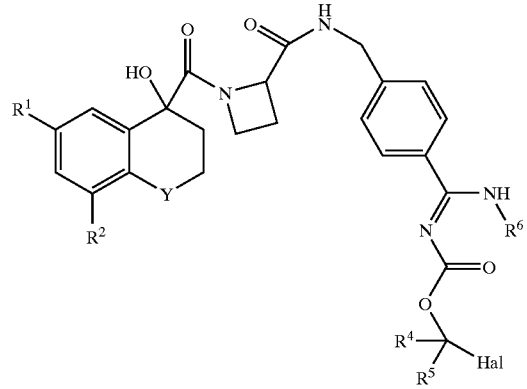

XXVI wherein Hal is as defined above and Y, $R^1$, $R^2$, $R^4$, $R^5$ and $R^6$ are as defined in claim 8;

(10) for compounds of formula IA in which $D^1$, $D^2$ and $R^3$, together with the amidine group to which they are attached, represent a group IIe as defined in claim 8, reaction of a corresponding compound of formula XXIX,

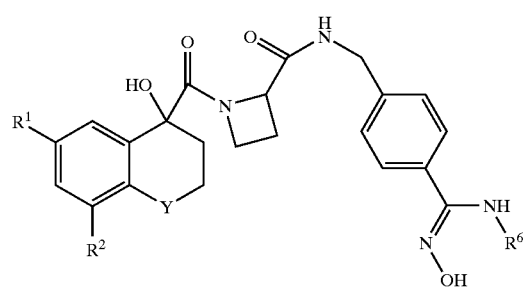

XXIX wherein Y, $R^1$, $R^2$ and $R^6$ are as defined in claim 8 with formaldehyde;

(11) deprotection of a protected compound of formula IA as defined in claim 8; or

(12) introduction or interconversion of a substituent on an aromatic and/or non-aromatic, carbocyclic and heterocyclic ring(s) in compounds of formula IA as defined in claim 8.

12. A pharmaceutical composition comprising a compound as claimed in claim 1, or a pharmaceutically acceptable salt or prodrug thereof, in admixture with a pharmaceutically acceptable adjuvant, diluent or carrier.

13. A method of treatment of a condition where inhibition of thrombin is required which method comprises administration of a therapeutically effective amount of a compound as claimed in claim 1, or a pharmaceutically acceptable salt or prodrug thereof, to a person suffering from, or susceptible to, such a condition.

14. A method as claimed in claim 13, wherein the condition is thrombosis.

15. A method as claimed in claim 13, wherein the condition is hypercoagulability in blood and/or tissues.

* * * * *

UNITED STATES PATENT AND TRADEMARK OFFICE
CERTIFICATE OF CORRECTION

PATENT NO. : 6,716,834 B2
DATED : April 6, 2004
INVENTOR(S) : Andersson et al.

It is certified that error appears in the above-identified patent and that said Letters Patent is hereby corrected as shown below:

Column 1,
Line 56, change "41 1" to -- 411 --;
Line 60, change "fibrinogen ⌗" to -- fibrinogen Aα --;
Line 65, "⌗ω-aminoalkyl" to -- α,ω-aminoalkyl --;

Column 2,
Line 33, change "⌗-keto" to -- α-keto --;
Line 35, change "⌗,⌗,⌗-triketocompounds" to -- α,ß,δ-triketocompounds --;
Line 36, change "⌗-alkoxy" to -- α-alkoxy --;
Line 59, delete the "," after "is";

Column 6,
Line 47, change "AD-mix-⌗$^{TM}$" to -- AD-mix-ß$^{TM}$ --;

Column 7,
Line 33, change "ORX" to -- OR$^x$ --;

Column 8,
Line 66, change "C(O)O$^{12}$" to -- C(O)OR$^{12}$ --;

Column 9,
Line 39, change "R$^{11a}$" to -- R$^{18a}$ --;

Column 16,
Line 17, "change "R$^1$" to -- R$^5$ --;

Column 20,
Lines 11, 12, 15, 41, 42, 45, 46 and 48, change each instance of "⌧L" to -- $\mu$L --;
Line 48, change "⌗-thrombin" to -- α-thrombin --;
Line 52, change "⌧mol/L" to -- $\mu$mol/L --;
Lines 53 and 66, change each instance of "⌗-thrombin" to -- α-thrombin --;

Column 21,
Lines 3, 4, 8, 9, 25, 26, 28, 64 and 65, change each instance of "⌧L" to -- $\mu$L --;
Line 5, change "⌗-thrombin" to -- α-thrombin --;
Line 11, change "(⌧A/min)" to -- (ΔA/min) --;
Line 17, change "⌧A/min)" to -- ΔA/min) --;
Line 35, change "(APTT$_1$)" to -- (APTT$_i$) --;

UNITED STATES PATENT AND TRADEMARK OFFICE
CERTIFICATE OF CORRECTION

PATENT NO. : 6,716,834 B2
DATED : April 6, 2004
INVENTOR(S) : Andersson et al.

It is certified that error appears in the above-identified patent and that said Letters Patent is hereby corrected as shown below:

Column 22,
Lines 1, 41 and 45, change each instance of "⊠L" to -- $\mu$L --;

Column 23,
Lines 11 and 14, change each instance of "⊠L" to -- $\mu$L --;

Column 24,
Line 11, change "Umea" to -- Umeå --;

Column 26,
Line 14, change "formnic" to -- formic --;

Column 32,
Line 50, change "saturate d" to -- saturated --;

Column 33,
Line 59, change "Buichner" to -- Büchner --;

Column 34,
Line 42, change "$^3$C" to -- $^{13}$C --;
Line 44, change "↯" to -- $\delta$ --;

Column 35,
Lines 4, 8, 27 and 42, change each instance of "↯" to -- $\delta$ --;

Column 36,
Lines 2 and 19, change each instance of "↯" to -- $\delta$ --;

Column 39,
Line 59, change "Ia" to -- IIa --; and

UNITED STATES PATENT AND TRADEMARK OFFICE
CERTIFICATE OF CORRECTION

PATENT NO. : 6,716,834 B2
DATED : April 6, 2004
INVENTOR(S) : Andersson et al.

It is certified that error appears in the above-identified patent and that said Letters Patent is hereby corrected as shown below:

Column 43,
Line 4, change "$(R^{8b})$" to -- $(R^{18b})$ --.

Signed and Sealed this

Tenth Day of August, 2004

JON W. DUDAS
*Acting Director of the United States Patent and Trademark Office*